US012716973B2

(12) United States Patent
Bydder et al.

(10) Patent No.: US 12,716,973 B2
(45) Date of Patent: Aug. 25, 2026

(54) SYSTEM AND METHOD FOR CONCURRENT X-NUCLEI AND H-NUCLEI MAGNETIC RESONANCE IMAGING

(71) Applicant: The Regents of the University of California, Oakland, CA (US)

(72) Inventors: Mark Bydder, Los Angeles, CA (US); Benjamin M. Ellingson, Redondo Beach, CA (US); Jingwen Yao, Los Angeles, CA (US)

(73) Assignee: The Regents of the University of California, Oakland, CA (US)

(*) Notice: Subject to any disclaimer, the term of this patent is extended or adjusted under 35 U.S.C. 154(b) by 274 days.

(21) Appl. No.: 18/546,188

(22) PCT Filed: Feb. 14, 2022

(86) PCT No.: PCT/US2022/016338

§ 371 (c)(1),
(2) Date: Aug. 11, 2023

(87) PCT Pub. No.: WO2022/174153

PCT Pub. Date: Aug. 18, 2022

(65) Prior Publication Data

US 2024/0125880 A1 Apr. 18, 2024

Related U.S. Application Data

(60) Provisional application No. 63/148,718, filed on Feb. 12, 2021.

(51) Int. Cl.
*G01R 33/561* (2006.01)
*A61B 5/00* (2006.01)
(Continued)

(52) U.S. Cl.
CPC ........ *G01R 33/5615* (2013.01); *A61B 5/0042* (2013.01); *A61B 5/055* (2013.01); *G01R 33/4818* (2013.01); *G01R 33/4828* (2013.01)

(58) Field of Classification Search
CPC ...... A61B 5/055; A61B 5/0263; A61B 8/0808
See application file for complete search history.

(56) References Cited

U.S. PATENT DOCUMENTS 9,451,917 B2 * 9/2016 Kaggie ................ A61B 5/4312
10,194,829 B2 * 2/2019 Kaditz .................. A61B 5/055
(Continued)

FOREIGN PATENT DOCUMENTS

WO 2013022333 A2 2/2013

OTHER PUBLICATIONS

International Searching Authority, International Search Report and Written Opinion issued for PCT/US2022/016338 dated Apr. 28, 2022.

(Continued)

*Primary Examiner* — Huy Q Phan
*Assistant Examiner* — Temilade S Rhodes-Vivour
(74) *Attorney, Agent, or Firm* — Quarles & Brady LLP

(57) ABSTRACT

A method for generating magnetic resonance (MR) images of a kidney region or a brain of a subject using multinuclear magnetic resonance imaging MRI includes performing, using an MRI system, an Na-nuclei pulse sequence module to acquire a portion of a first set of MR data from the kidney or brain region of the subject and performing, using the MRI system, an H-nuclei pulse sequence module to acquire a portion of a second set of MR data from the kidney or brain region of the subject. The Na-nuclei pulse sequence module and the H-nuclei pulse sequence module may be repeated in an interleaved manner until acquisition of the first set of MR data and the second set of MR data are complete. The (Continued)

method further includes generating at least one Na-based image using the first set of MR data, generating at least one H-based image using the second set of MR data and displaying one or more of the at least one Na-based image and the at least one H-based image on a display.

20 Claims, 14 Drawing Sheets

(51) Int. Cl.
*A61B 5/055* (2006.01)
*G01R 33/48* (2006.01)

(56) References Cited

U.S. PATENT DOCUMENTS

| | | | | |
|---|---|---|---|---|
| 2006/0062731 | A1* | 3/2006 | Bammer | A61B 5/0263 424/9.3 |
| 2013/0096415 | A1 | 4/2013 | Ruff et al. | |
| 2013/0204123 | A1* | 8/2013 | Feinberg | A61B 5/055 600/419 |
| 2015/0247910 | A1* | 9/2015 | Riederer | G01R 33/5619 324/309 |
| 2015/0362569 | A1 | 12/2015 | Kaggie et al. | |
| 2017/0007148 | A1 | 1/2017 | Kaditz et al. | |
| 2018/0164393 | A1 | 6/2018 | Ellingson et al. | |
| 2018/0268942 | A1 | 9/2018 | Kamali-Zare et al. | |
| 2018/0292488 | A1* | 10/2018 | Moeller | G01R 33/5616 |
| 2020/0158803 | A1 | 5/2020 | Harris et al. | |

OTHER PUBLICATIONS

International Searching Authority, International Preliminary Report on Patentability issued for PCT/US2022/016338 dated Aug. 15, 2023.
Atkinson, D., et al., "Automatic Correction of Motion Artefacts in Magnetic Resonance Images Using an Entropy Focus Criterion" IEEE Trans Med Imaging (1997) 16(6): 903-910.
Bilgic, B., et al., "Improving parallel imaging by jointly reconstructing multi-contrast data" Magn Reson Med. (2018) 80(2): 619-32.
Bottomley, P.A., "Sodium MRI in Man: Technique and Findings" eMagRes (2012) vol. 1, p. 353-366 DOI 10.1002/9780470034590.emrstm1252.
Bydder, M., et al., "Noise reduction in multiple-echo data sets using singular value decomposition" Magn Reson Imaging. (2006) 24(7): 849-856.
Bydder, M., et al., "Trimmed autocalibrating k-space estimation based on structured matrix completion" Magn Reson Imaging (2017) 43: 88-94.
Bydder, M., et al., "Minimizing echo and repetition times in magnetic resonance imaging using a double half-echo k-space acquisition and low-rank reconstruction" NMR Biomed. (2021) 34(4):e4458.
Campbell-Washburn, AE, et al., "Using the robust principal component analysis algorithm to remove RF spike artifacts from MR images" Magn Reson Med. (2016) 75: 2517-2525.
Ghodrati, V., et al., "Retrospective respiratory motion correction in cardiac cine MRI reconstruction using adversarial autoencoder and unsupervised learning" NMR Biomed. (2021) 34: e4433.
Gonen, O., et al., "Simultaneous and Interleaved Multinuclear Chemical-Shift Imaging, a Method for Concurrent, Localized Spectroscopy" J. Mag. Reson. (1994) Series B 104, 26-33.
Haldar, JP "Low-rank modeling of local k-space neighborhoods for constrained MRI" IEEE Trans Med Imaging. (2014) 33(3):668-681.
Jiang, W., et al., "Simultaneous auto-calibration and gradient delays estimation in non-Cartesian parallel MRI using low-rank constraints" Magn Reson Med. (2018) 80(5):2006-2016.
Jin, K., et al., "MRI artifact correction using sparse+low rank decomposition of annihilating filter based hankel matrix" Magn Reson Med. (2017) 78(1): 327-340.
Jones, S.C., et al., "Stroke Onset Time Using Sodium MRI in Rat Focal Cerebral Ischemia" Stroke (2006) 37:883-888.
Lee, S.W., et al., "A Multinuclear Magnetic Resonance Imaging Technique-Simultaneous Proton and Sodium Imaging" Mag, Reson. Imaging (1986) vol. 4, pp. 343-350.
Lee, D., et al., "Acceleration of MR parameter mapping using annihilating filter-based low rank hankel matrix" Magn Reson Med (2016) 76: 1848-1864.
Lee, J., et al., "Reference-free single-pass EPI Nyquist ghost correction using annihilating filter-based low rank Hankel matrix" Magn Reson Med. (2016) 76(6):1775-1789.
Lobos, RA, et al., "Robust autocalibrated structured low-rank EPI ghost correction" Magn Reson Med. (2021) 85(6): 3403-3419.
Madelin, G., et al., "Biomedical Applications of Sodium MRI In Vivo" J Magn Reson Imaging. (2013) 38:511-529.
Meyerspeer, M., et al., "Simultaneous and Interleaved Acquisition of NMR Signals from Different Nuclei with a Clinical MRI Scanner" Mag. Reson. Med. (2016) 76:1636-1641.
Nagel, A.M., et al., "Sodium MRI Using a Density-Adapted 3D Radial Acquisition Technique" Magn. Reson. Med. (2009) 62 p. 1565-1573.
Neumaier-Probst, E., et al., "A double-tuned 1H/23Na resonator allows 1H-guided 23Na-MRI in ischemic stroke patients in one session" International Journal of Stroke (2015) 10:56-61.
Ogier, S., et al., "A Broadband Spectrometer for Simultaneous Multinuclear Magnetic Resonance Imaging and Spectroscopy" 2016 https://archive.ismrm.org/2016/0546.html.
Scheidegger, MB, et al., "FID-Acquired-Echos: A short echo time imaging method for flow artefact suppression" Magn Reson Imaging (1991) 9(4): 517-524.
Shin, PJ, et al., "Calibrationless parallel imaging reconstruction based on structured low-rank matrix completion" Magn Reson Med. (2014) 72(4):959-970.
Tamir, JI, et al., "T2 shuffling: Sharp, multicontrast, volumetric fast spin-echo imaging" Magn Reson Med. (2017) 77 (1): 180-195.
Thulborn, K.R., "Quantitative sodium MR imaging: A review of its evolving role in medicine" NeuroImage (2018) 168 p. 250-268.
Wetterling, F., et al., "Regional and Temporal Variations in Tissue Sodium Concentration During the Acute Stroke Phase" Magnetic Resonance in Medicine (2012) 67:740-749.
Yu, Z., et al., "Simultaneous Proton Magnetic Resonance Fingerprinting and Sodium MRI" Mag. Reson. In Med. (2020) 83(6): 2232-2242 DOI: 10.1002/mrm.28073.

* cited by examiner

ERNST ANGLE (SPOILED)
X NUCLEUS
30°
502
GRADIENT ECHO READOUT
504
TE 1 (center out)
500
20x
X-SBB$_{EA}$ bSSFP (BALANCED)
X NUCLEUS
60°
602
604
600
15x
X-SBB$_{SS}$

SYSTEM AND METHOD FOR CONCURRENT X-NUCLEI AND H-NUCLEI MAGNETIC RESONANCE IMAGING

CROSS-REFERENCE TO RELATED APPLICATIONS

This application represents the national stage entry of PCT/US2022/016338 filed Feb. 14, 2022 and is based on, claims priority to, and incorporates herein by reference in its entirety U.S. Ser. No. 63/148,718 filed Feb. 12, 2021 and entitled "System and Method for Concurrent X-Nuclei and H-Nuclei Magnetic Resonance Imaging".

BACKGROUND

Magnetic resonance imaging (MRI) is clinically performed on hydrogen (H) nuclei as it is the most abundant element in the human body in the form of water. However, other nuclei are also visible with MRI. These are referred to as X-nuclei, where X can stand for several different elements. Potentially useful elements (X) for medical imaging are sodium (Na), fluorine (F) and phosphorous (P), each of which play key roles in biochemistry. However, the relative low abundance of X-nuclei compared to hydrogen nuclei makes them difficult to see above the background noise. While hydrogen protons have a concentration of about 110 M in the body, the next most abundant, sodium (Na), is in the tens of mM, i.e., a factor of 10,000 lower. To achieve adequate signal levels for X-nuclei, such as sodium, necessitates low spatial resolution and long measurement times by averaging many times. Averaging increases the signal linearly while noise adds as the square root, leading to an overall improvement in signal to noise ratio (SNR) as the square root of number of averages. The square root increase in SNR with linear increase in scan time is particularly challenging when trying to overcome a factor of 10000. In principle, to match the SNR of a 1-minute hydrogen proton scan would require the sodium scan to last for 190 years. This is, however, unfeasible and researchers have spent considerable effort in optimizations to claw back numerous small factors of 2-4 by reductions in spatial resolution and others forms of averaging (low bandwidth, multiple echo combination, steady state imaging with short repetition times), as well as hardware improvements. Typical X-nucleus scan times, incorporating all these compromises, are on the order of 30 minutes, which is comparable to the time for a clinical MRI examination of hydrogen.

X-nucleus imaging is never done in isolation but always in conjunction with proton imaging so the total time can add up to an hour. A recent study (Zidan Yu, Guillaume Madelin, Daniel K. Sodickson, Martijn A. Cloos, "Simultaneous proton magnetic resonance fingerprinting and sodium MRI," Mag. Reson. in Med. 2019) described perfectly synchronous hydrogen and X-nucleus imaging, in which identical instructions were sent to both imaging nuclei. This is efficient but of limited clinical value since it requires the same pattern of instructions (or "sequence" in MRI terminology) to be transmitted to the H- and X-nuclei. Clinical imaging uses many different sequences that are sensitive to different lesion types so it would be clinically a non-starter to limit the H-imaging component this way.

SUMMARY

In accordance with an embodiment, a method for generating magnetic resonance (MR) images of a kidney region of a subject using multinuclear magnetic resonance imaging (MRI) includes performing, using an MRI system, a Na-nuclei pulse sequence module to acquire a portion of a first set of MR data from the kidney region of the subject and performing, using the MRI system, an H-nuclei pulse sequence module to acquire a portion of a second set of MR data from the kidney region of the subject. The Na-nuclei pulse sequence module and the H-nuclei pulse sequence module may be repeated in an interleaved manner until acquisition of the first set of MR data and the second set of MR data are complete. The method further includes generating at least one Na-based image using the first set of MR data, generating at least one H-based image using the second set of MR data and displaying one or more of the at least one Na-based image and the at least one H-based image on a display.

In accordance with another embodiment, a method for generating magnetic resonance (MR) images of a brain of a subject using multinuclear magnetic resonance imaging (MRI) includes performing a Na-nuclei pulse sequence module to acquire a portion of a first set of MR data from the brain of the subject and performing an H-nuclei pulse sequence module to acquire a portion of a second set of MR data from the brain of the subject. The Na-nuclei pulse sequence module and the H-nuclei pulse sequence module may be repeated in an interleaved manner until acquisition of the first set of MR data and the second set of MR data are complete. The method further includes generating at least one Na-based image using the first set of MR data, generating at least one H-base image using the second set of MR data and displaying one or more of the at least one Na-based image and the at least one H-based image.

In accordance with another embodiment, a method for generating magnetic resonance (MR) images of a brain of a subject using multinuclear magnetic resonance imaging (MRI) includes performing a Na-nuclei pulse sequence module to acquire a portion of a first set of MR data from the brain of the subject and performing an H-nuclei pulse sequence module to acquire a portion of a second set of MR data from the brain of the subject, wherein the H-nuclei pulse sequence module includes a preparation module. The Na-nuclei pulse sequence module and the H-nuclei pulse sequence module may be repeated in an interleaved manner until acquisition of the first set of MR data and the second set of MR data are complete. The method further includes generating at least one Na-based image using the first set of MR data, generating at least one H-base image using the second set of MR data and displaying one or more of the at least one Na-based image and the at least one H-based image.

BRIEF DESCRIPTION OF THE DRAWINGS

The present invention will hereafter be described with reference to the accompanying drawings, wherein like reference numerals denote like elements.

DETAILED DESCRIPTION

Figure 1:
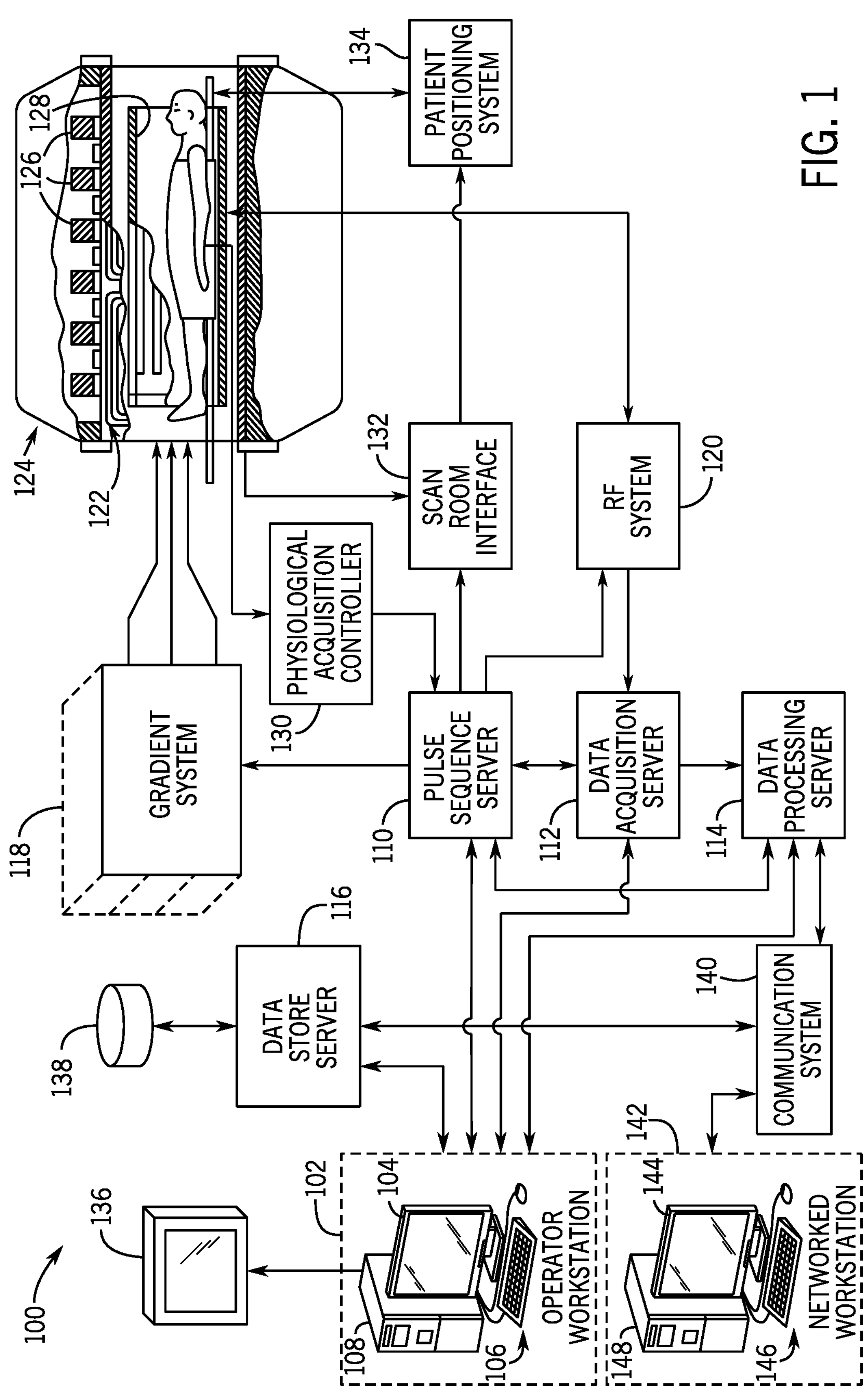
FIG. 1 is a schematic diagram of an example MRI system in accordance with an embodiment.

FIG. 1 shows an example of an MRI system 100 that may be used to perform the methods described herein. MRI system 100 includes an operator workstation 102, which may include a display 104, one or more input devices 106 (e.g., a keyboard, a mouse), and a processor 108. The processor 108 may include a commercially available programmable machine running a commercially available operating system. The operator workstation 102 provides an operator interface that facilitates entering scan parameters into the MRI system 100. The operator workstation 102 may be coupled to different servers, including, for example, a pulse sequence server 110, a data acquisition server 112, a data processing server 114, and a data store server 116. The operator workstation 102 and the servers 110, 112, 114, and 116 may be connected via a communication system 140, which may include wired or wireless network connections.

The pulse sequence server 110 functions in response to instructions provided by the operator workstation 102 to operate a gradient system 118 and a radiofrequency ("RF") system 120. Gradient waveforms for performing a prescribed scan are produced and applied to the gradient system 118, which then excites gradient coils in an assembly 122 to produce the magnetic field gradients $G_x$, $G_y$, and $G_z$ that are used for spatially encoding magnetic resonance signals. The gradient coil assembly 122 forms part of a magnet assembly 124 that includes a polarizing magnet 126 and a whole-body RF coil 128.

RF waveforms are applied by the RF system 120 to the RF coil 128, or a separate local coil to perform the prescribed magnetic resonance pulse sequence. Responsive magnetic resonance signals detected by the RF coil 128, or a separate local coil, are received by the RF system 120. The responsive magnetic resonance signals may be amplified, demodulated, filtered, and digitized under direction of commands produced by the pulse sequence server 110. The RF system 120 includes an RF transmitter for producing a wide variety of RF pulses used in MRI pulse sequences. The RF transmitter is responsive to the prescribed scan and direction from the pulse sequence server 110 to produce RF pulses of the desired frequency, phase, and pulse amplitude waveform. The generated RF pulses may be applied to the whole-body RF coil 128 or to one or more local coils or coil arrays.

The RF system 120 also includes one or more RF receiver channels. An RF receiver channel includes an RF preamplifier that amplifies the magnetic resonance signal received by the coil 128 to which it is connected, and a detector that detects and digitizes the I and Q quadrature components of the received magnetic resonance signal. The magnitude of the received magnetic resonance signal may, therefore, be determined at a sampled point by the square root of the sum of the squares of the I and Q components:

$$M=\sqrt{I^2+Q^2}; \qquad \text{Eqn. 1}$$

and the phase of the received magnetic resonance signal may also be determined according to the following relationship:

$$\varphi=\tan^{-1}\left(\frac{Q}{I}\right). \qquad \text{Eqn 2}$$

The pulse sequence server 110 may receive patient data from a physiological acquisition controller 130. By way of example, the physiological acquisition controller 130 may receive signals from a number of different sensors connected to the patient, including electrocardiograph ("ECG") signals from electrodes, or respiratory signals from a respiratory bellows or other respiratory monitoring devices. These signals may be used by the pulse sequence server 110 to synchronize, or "gate," the performance of the scan with the subject's heart beat or respiration.

The pulse sequence server 110 may also connect to a scan room interface circuit 132 that receives signals from various sensors associated with the condition of the patient and the magnet system. Through the scan room interface circuit 132, a patient positioning system 134 can receive commands to move the patient to desired positions during the scan.

The digitized magnetic resonance signal samples produced by the RF system 120 are received by the data acquisition server 112. The data acquisition server 112 operates in response to instructions downloaded from the operator workstation 102 to receive the real-time magnetic resonance data and provide buffer storage, so that data is not lost by data overrun. In some scans, the data acquisition server 112 passes the acquired magnetic resonance data to the data processor server 114. In scans that require information derived from acquired magnetic resonance data to control the further performance of the scan, the data acquisition server 112 may be programmed to produce such information and convey it to the pulse sequence server 110. For example, during pre-scans, magnetic resonance data may be acquired and used to calibrate the pulse sequence performed by the pulse sequence server 110. As another example, navigator signals may be acquired and used to adjust the operating parameters of the RF system 120 or the gradient system 118, or to control the view order in which k-space is sampled. In still another example, the data acquisition server 112 may also process magnetic resonance signals used to detect the arrival of a contrast agent in a magnetic resonance angiography ("MRA") scan. For example, the data acquisition server 112 may acquire magnetic resonance data and processes it in real-time to produce information that is used to control the scan.

The data processing server 114 receives magnetic resonance data from the data acquisition server 112 and processes the magnetic resonance data in accordance with instructions provided by the operator workstation 102. Such processing may include, for example, reconstructing two-dimensional or three-dimensional images by performing a Fourier transformation of raw k-space data, performing other image reconstruction algorithms (e.g., iterative or backprojection reconstruction algorithms), applying filters to raw k-space data or to reconstructed images, generating functional magnetic resonance images, or calculating motion or flow images.

Images reconstructed by the data processing server 114 are conveyed back to the operator workstation 102 for storage. Real-time images may be stored in a data base memory cache, from which they may be output to operator display 104 or a display 136. Batch mode images or selected real time images may be stored in a host database on disc storage 138. When such images have been reconstructed and transferred to storage, the data processing server 114 may notify the data store server 116 on the operator workstation 102. The operator workstation 102 may be used by an operator to archive the images, produce films, or send the images via a network to other facilities.

The MRI system 100 may also include one or more networked workstations 142. For example, a networked workstation 142 may include a display 144, one or more input devices 146 (e.g., a keyboard, a mouse), and a processor 148. The networked workstation 142 may be located within the same facility as the operator workstation 102, or in a different facility, such as a different healthcare institution or clinic.

The networked workstation 142 may gain remote access to the data processing server 114 or data store server 116 via the communication system 140. Accordingly, multiple networked workstations 142 may have access to the data processing server 114 and the data store server 116. In this manner, magnetic resonance data, reconstructed images, or other data may be exchanged between the data processing server 114 or the data store server 116 and the networked workstations 142, such that the data or images may be remotely processed by a networked workstation 142.

The present disclosure describes an approach to imaging H-nuclei and X-nuclei at the same time. The described embodiments for multinuclear MRI imaging methods involve various ways of interleaving the sets of instructions (or modules or sequence building blocks (SBB)) that are used on the H-nuclei and the X-nuclei during a scan. Interleaving the H-nuclei pulse sequence modules (or SBBs) and the X-nuclei pulse sequence modules (or SBBs) retains the flexibility to perform independent sequences on each nucleus using the MRI scanner. As used herein, the terms H-SBB, H-nuclei module, or H-nuclei pulse sequence module refer to a unit of a hydrogen imaging sequence and the terms X-SBB, X-nuclei module, or X-nuclei pulse sequence module refer to a unit of the X-nucleus imaging sequence. In an embodiment, the present disclosure describes methods for interleaved and simultaneous $Na^+$ and $H^+$ acquisition (where the X-nuclei is Na). In particular, Na-nuclei and H-nuclei modules (or SBBs) are designed that can be put together to build a single multinuclear pulse sequence and, for example, cut sequence time by approximately 50%. In various embodiments, the multinuclear sequence with interleaved X-nuclei and H-nuclei modules (or SBBs) may be used in various imaging applications, such as evaluating renal impairment, stroke, epilepsy, and brain tumors. While the following description will refer to embodiments where sodium (Na) is the X-nuclei, it should be understood that the methods described herein may be used for imaging other X-nuclei, such as fluorine (F) and phosphorous (P), in multinuclear MRI imaging.

Figure 2:
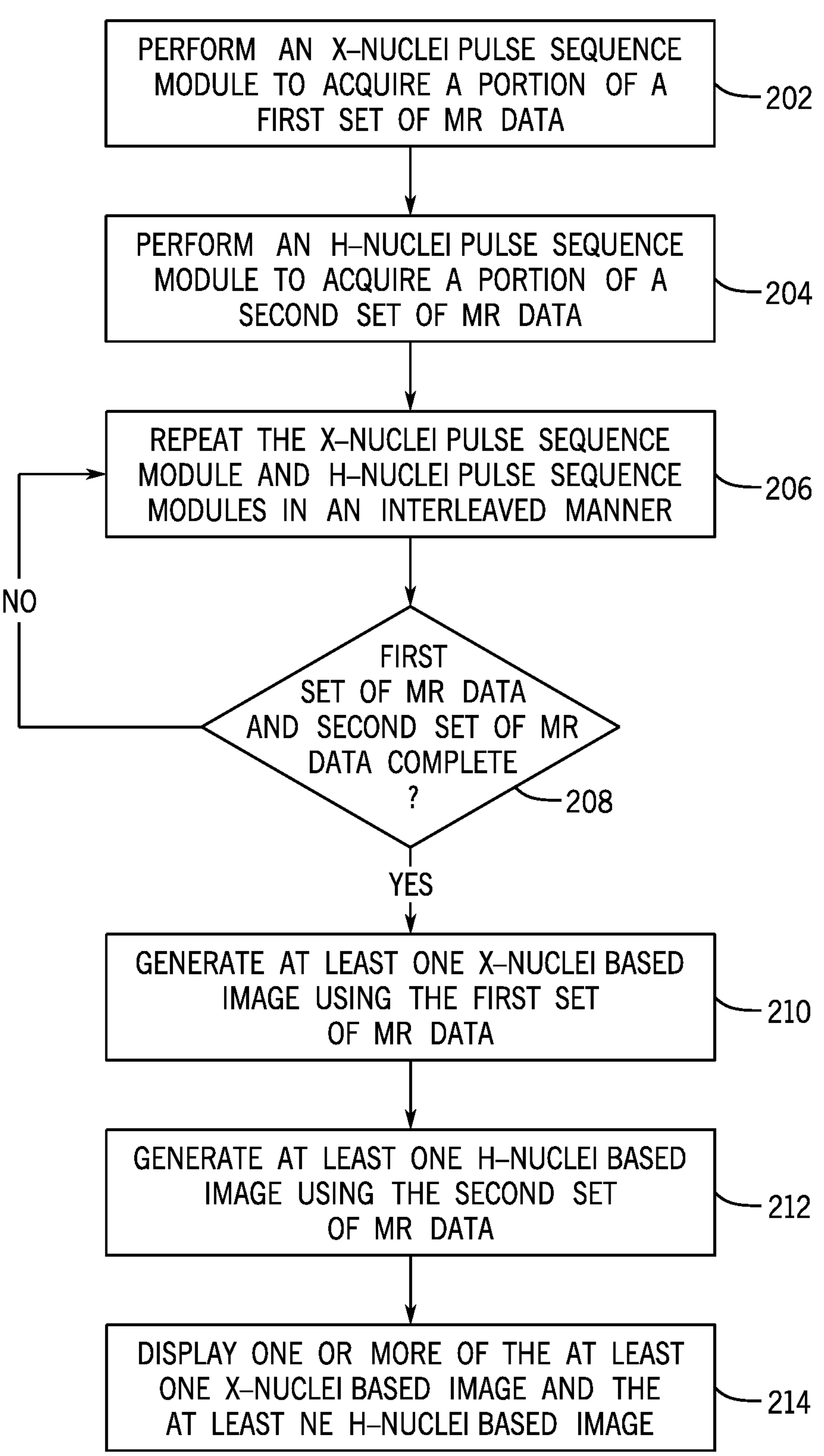
FIG. 2 illustrates a method for multinuclear MR imaging in accordance with an embodiment.
Figure 4:
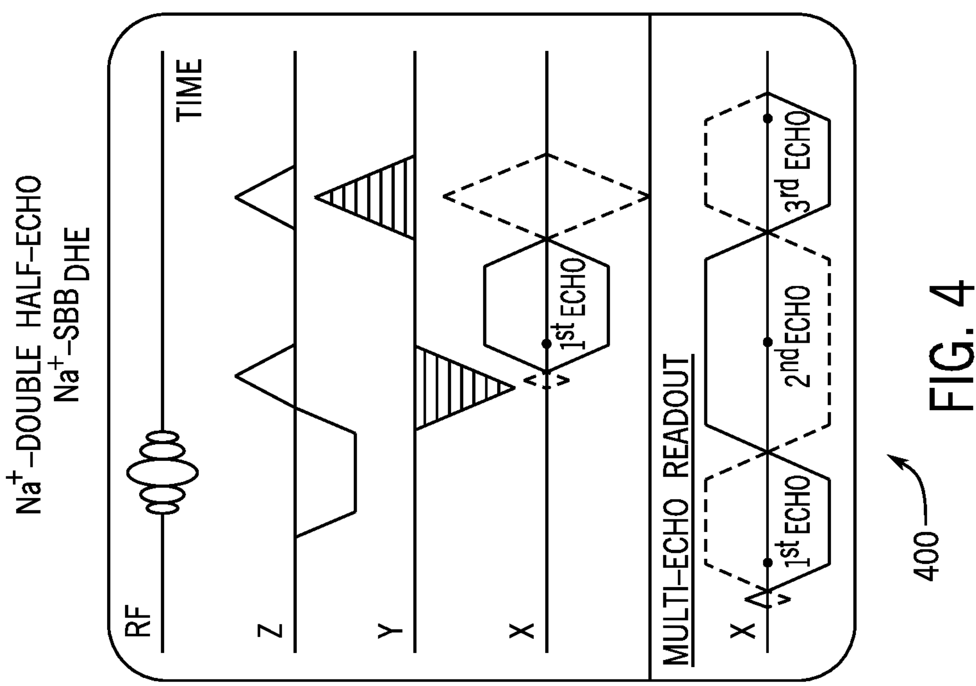
FIG. 4 illustrates an example double half-echo X-nuclei pulse sequence module in accordance with an embodiment.
Figure 3:
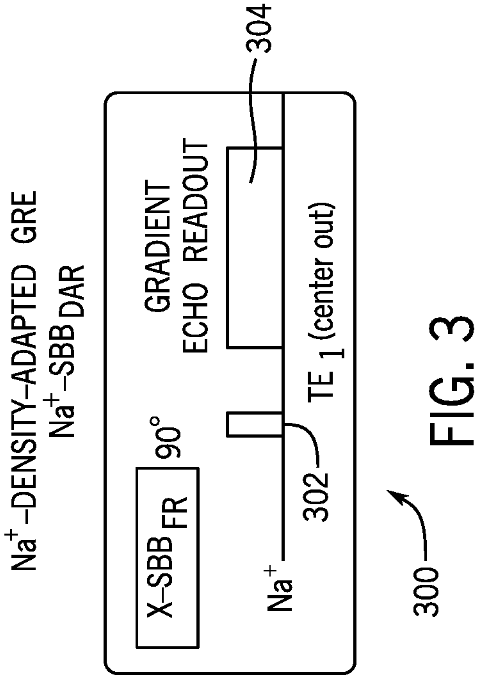
FIG. 3 illustrates an example density-adapted GRE X-nuclei pulse sequence module in accordance with an embodiment.
Figures 5, 6:
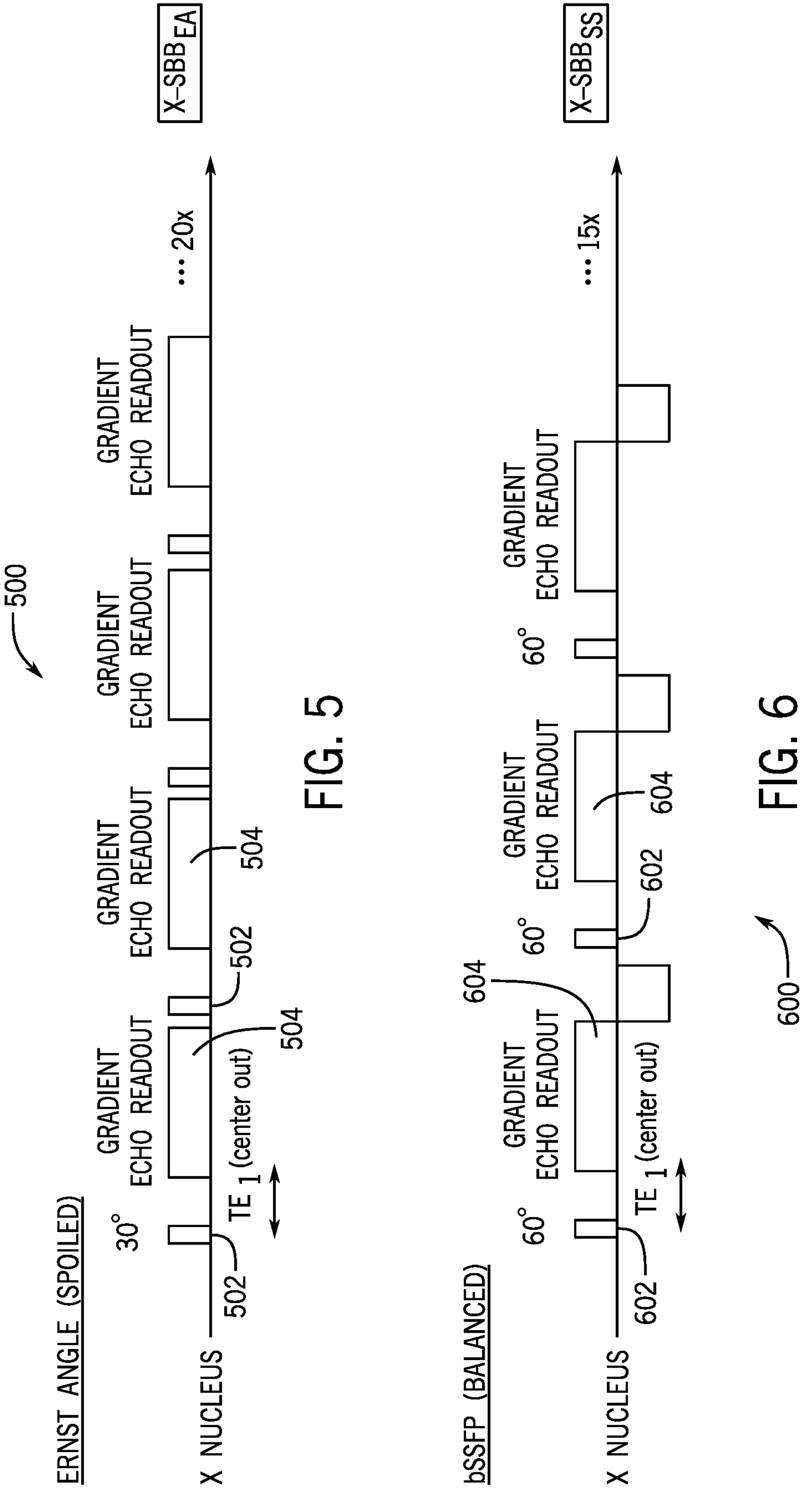
FIG. 5 illustrates an example Ernst angle (spoiled) X-nuclei pulse sequence module in accordance with an embodiment.
FIG. 6 illustrates an example balanced steady-state free precession (bSSFP) X-nuclei pulse sequence module in accordance with an embodiment.

FIG. 2 illustrates a method for multinuclear MR imaging in accordance with an embodiment. At block 202, an X-nuclei pulse sequence module (or SBB) may be performed using an MRI system (e.g., MRI system 100 described above with respect to FIG. 1) to acquire a portion of a first set of MR data from a region of interest in a subject. For example, in the following description, the X-nuclei is sodium (Na-nuclei). The first set of MR data may be acquired using a first RF coil that is tuned to the X-nuclei. The Na-nuclei pulse sequence module (or SBB) may take various forms, for example, as shown in FIGS. 3-6. In FIG. 3, an example Na-Density Adapted GRE (DAR) sequence building block or module ($Na^+$-$SBB_{DAR}$) 300 is shown. In FIG. 3, a 90° excitation RF pulse 302 is followed by a gradient echo readout 304. In the example module 300, the readout trajectory is center out. In some embodiments, the gradients of the density-adapted radial projection can be designed such that the outer k-space has a constant sampling density in each spherical shell. In FIG. 4, an example Na-Double Half-Echo (DHE) sequence building block or module ($Na^+$-$SBB_{DHE}$) 400 is shown. In FIG. 5, an example X- (e.g., Na) Ernst Angle (EA), spoiled, sequence building block or module (X-$SBB_{EA}$) 500 is shown. In FIG. 5, a 30° excitation RF pulse 502 is followed by a gradient echo readout 504. In the example module 500, the readout trajectory is center out. The RF pulse 502 and gradient echo readout 504 can be repeatedly applied. To ensure no transverse component of the magnetization at the beginning of the cycles, spoiling can be implemented with an additional spoiler gradient after readout module 504, or changing phase of the RF pulse module from acquisition to acquisition. In FIG. 6, an example X-Balanced Steady-State Free Precession (bSSFP) sequence building block or module (Z-$SBB_{SS}$) is shown. In FIG. 6, a 60° excitation RF pulse 602 is followed by a gradient echo readout 604. In the example module 600, the readout trajectory is center out. The RF pulse 602 and gradient echo readout 604 can be repeatedly applied. Compared to module 504 shown in FIG. 5, module 604 can include a refocusing gradient after readout to ensure zero gradient-induced dephasing over the repetition time interval.

Figures 7, 8:
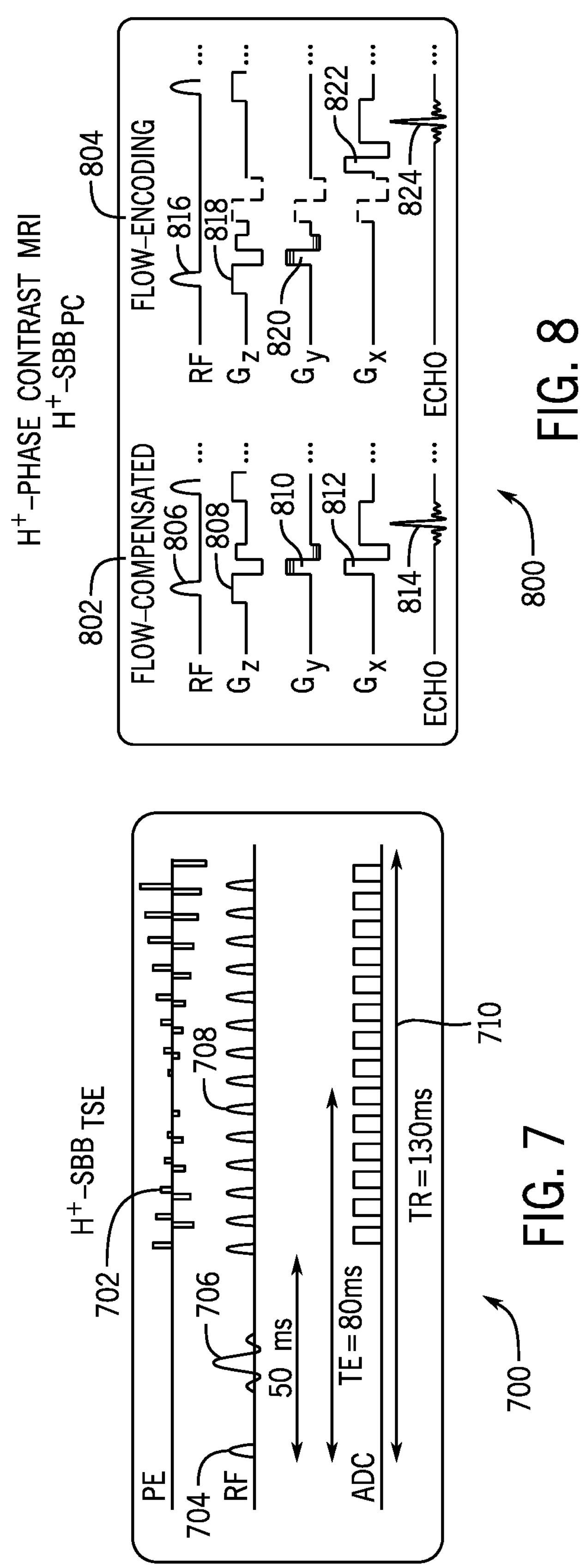
FIG. 7 illustrates an example turbo spin echo (TSE) H-nuclei pulse sequence module in accordance with an embodiment.
FIG. 8 illustrates an example phase contrast (PC) MRI H-nuclei pulse sequence module in accordance with an embodiment.

Returning to FIG. 2, at block 204 an H-nuclei pulse sequence module (or SBB) may be performed using the MRI system (e.g., MRI system 100 described above with respect to FIG. 1) to acquire a portion of a second set of MR data from the region of interest in the subject. The second set of MR data may be acquired using a second RF coil that is tuned to the H-nuclei. The MRI system (e.g., MRI system 100 described above with respect to FIG. 1) is configured to switch between the first RF coil tuned to the X-nuclei and the second RF coil tuned to the H-nuclei. The H-nuclei pulse sequence module (or SBB) may take various forms, for example, as shown in FIGS. 7-12. In FIG. 7, an example $H^+$—Turbo Spin Echo (TSE) sequence building block or module ($H^+$—$SBBT_{TSE}$) 700 is shown. In this example, an excitation RF pulse 704 and a refocusing RF pulse 706 are played out consecutively, followed by a readout of multiple k-space lines, represented by the RF pulse 708, phase encoding gradient 702, and readout ADC 710. In FIG. 8, an example H-Phase Contrast (PC) MRI sequence building block or module ($H^+$-$SBB_{PC}$) 800 is shown. In the flow component 802, an excitation RF pulse 806 is played out with the slice-selection gradient 808, followed by phase-encoding gradient 810, readout gradient 812, and readout ADC 814. Compared to normal gradient echo sequences, the gradient modules 808, 810, and 812 can be characterized by an additional gradient lobe added prior to signal readout to compensate for motion-induced dephasing of the time of echo. In the flow-encoding module 804, similarly, an excitation RF pulse 816 is played out with the slice-selection gradient 818, followed by phase-encoding gradient 820, readout gradient 822, and readout ADC 824. Compared to the flow-compensated module 802, the gradient modules 818, 820, and 822 can be characterized by an additional pair of bipolar gradients (shown with dashed lines) to induce a phase shift in moving spins.

Figures 9, 10:
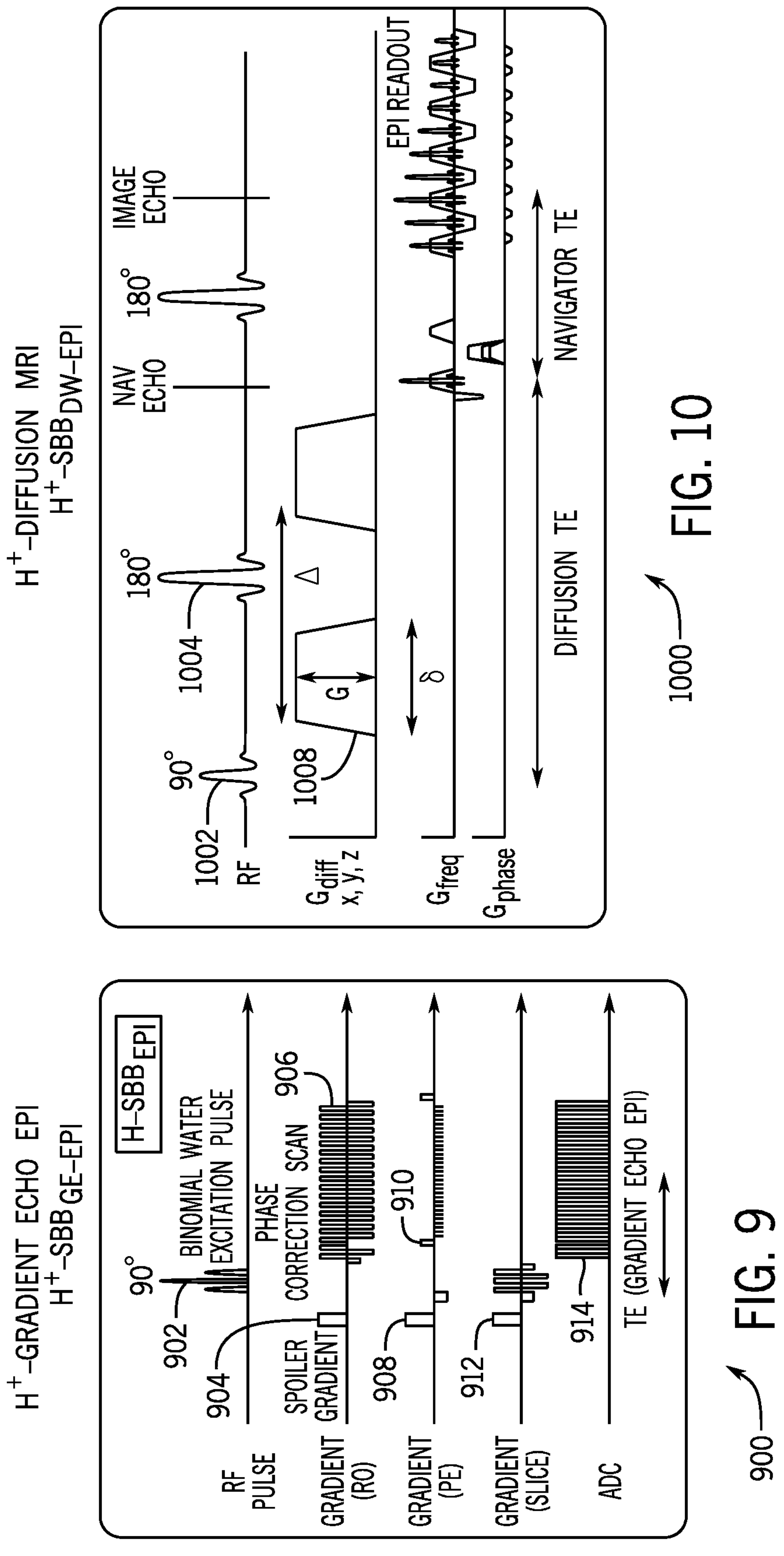
FIG. 9 illustrates an example gradient echo EPI H-nuclei pulse sequence module in accordance with an embodiment.
FIG. 10 illustrates an example diffusion MRI H-nuclei pulse sequence module in accordance with an embodiment.
Figure 11:
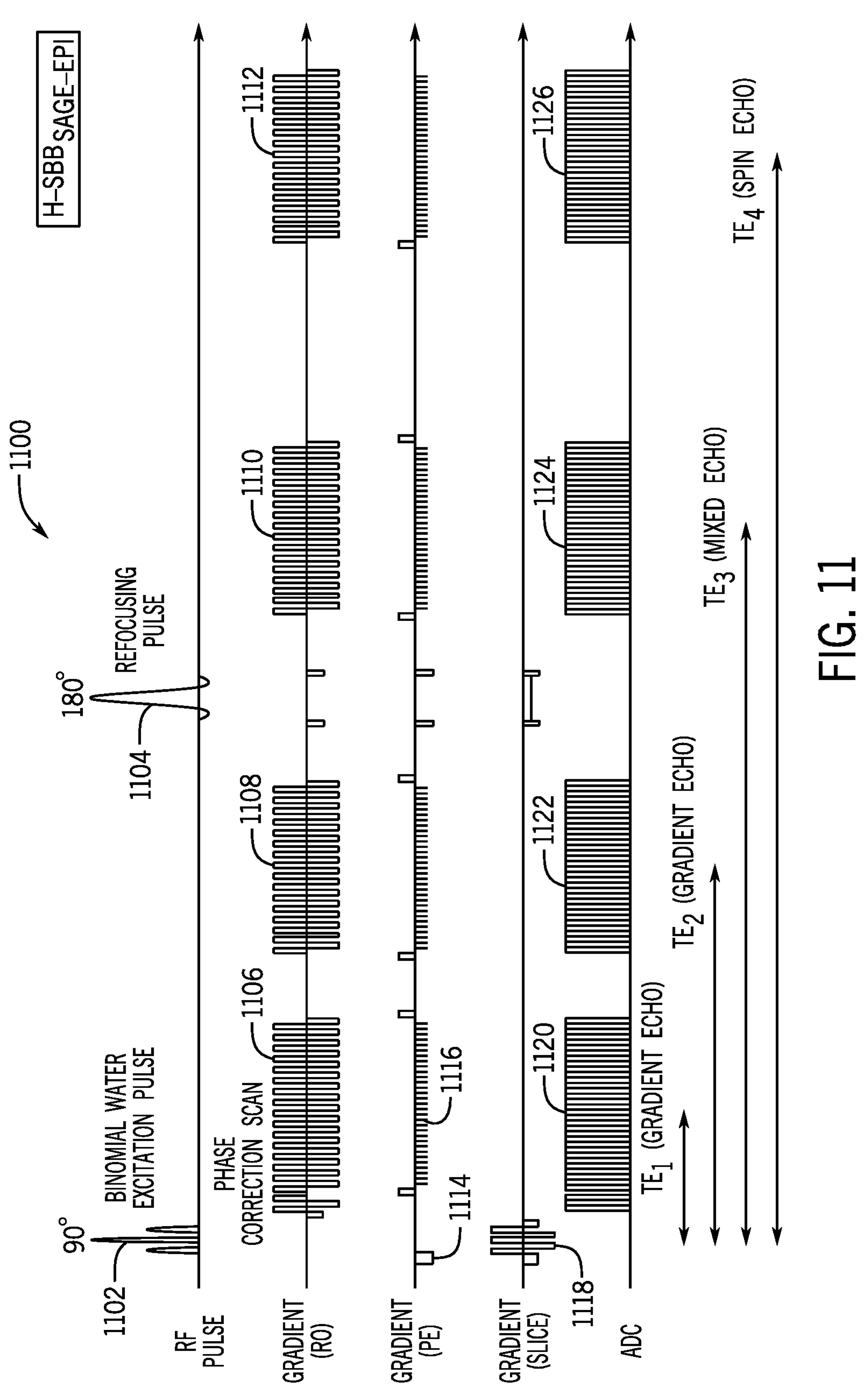
FIG. 11 illustrates an example SAGE-EPI H-nuclei pulse sequence module in accordance with an embodiment.
Figure 12:
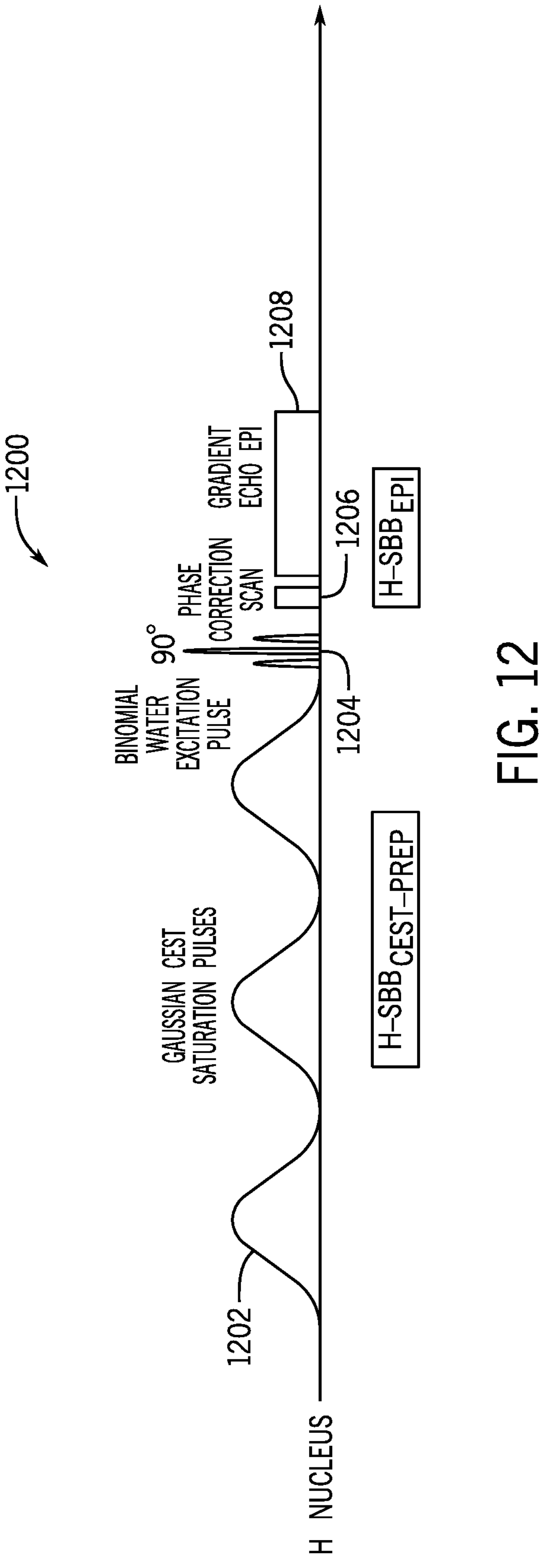
FIG. 12 illustrates an example EPI with CEST magnetization preparation H-nuclei pulse sequence module in accordance with an embodiment.

In FIG. 9, an example H-Gradient Echo (GE) Echo Planar Imaging (EPI) sequence building block or module ($H^+$-$SBB_{GE-EPI}$) 900 is shown. In this example, a 90° RF binomial water excitation pulse 902 is played out with the slice-selection gradient, followed by an EPI readout with phase-encoding gradient 910, readout gradient 906, and readout ADC 914. In addition, a phase correction acquisition can be performed immediately before the readout. Spoiler gradients 904, 908, and 912 in three gradient directions are applied at the end of each repetition time interval, before the next excitation pulse. In FIG. 10, an example H-Diffusion Weighted (DW) EPI sequence building block or module ($H^+$-$SBB_{DW-EPI}$) 1000 is shown. In this example, a 90° excitation pulse 1002 is followed by the diffusion gradients 1008, which is played before and after a refocusing RF pulse 1004. In FIG. 11, an example H-Spin and Gradient Echo (SAGE) EPI sequence building block or module ($H^+$-$SBB_{SAGE-EPI}$) 1100 is shown. In this example, a 90° RF binomial water excitation pulse 1102 is played out with the slice-selection gradients 1118, followed by the EPI readout at the first echo time (TE1) with phase-encoding gradients 1116, readout gradients 1106, and readout ADC 1120. After that, a second EPI readout at the second echo time (TE2) is performed with phase-encoding gradients 1116, readout gradients 1108, and readout ADC 1122. Following the second EPI readout, a 180° refocusing pulse is executed before the acquisition of the EPI readout of the third echo time (TE3), with phase-encoding gradients 1116, readout gradients 1110, and readout ADC 1124. Lastly, the EPI is acquired at the fourth echo time 1126. Similar to EPI module 900, a phase correction acquisition is performed immediately before the readout of the first EPI. Spoiler gradient 1114 is applied at the end of each repetition time interval, before the next excitation pulse. In FIG. 12, an example Chemical Exchange Saturation Transfer (CEST) preparation ($H^+$-$SBB_{CEST-Prep}$) and EPI ($H^+$-$SBB_{EPT}$) sequence building block or module 1200 is shown. In this example, CEST preparation can be performed with a train of non-selective gaussian saturation pulses 1202. The CEST preparation ($H^+$-$SBB_{CEST-Prep}$) is followed by the EPI ($H^+$-$SBB_{EPI}$) module as described above, with excitation pulse 1204, phase correction acquisition 1206, and EPI readout 1208.

Figure 13:
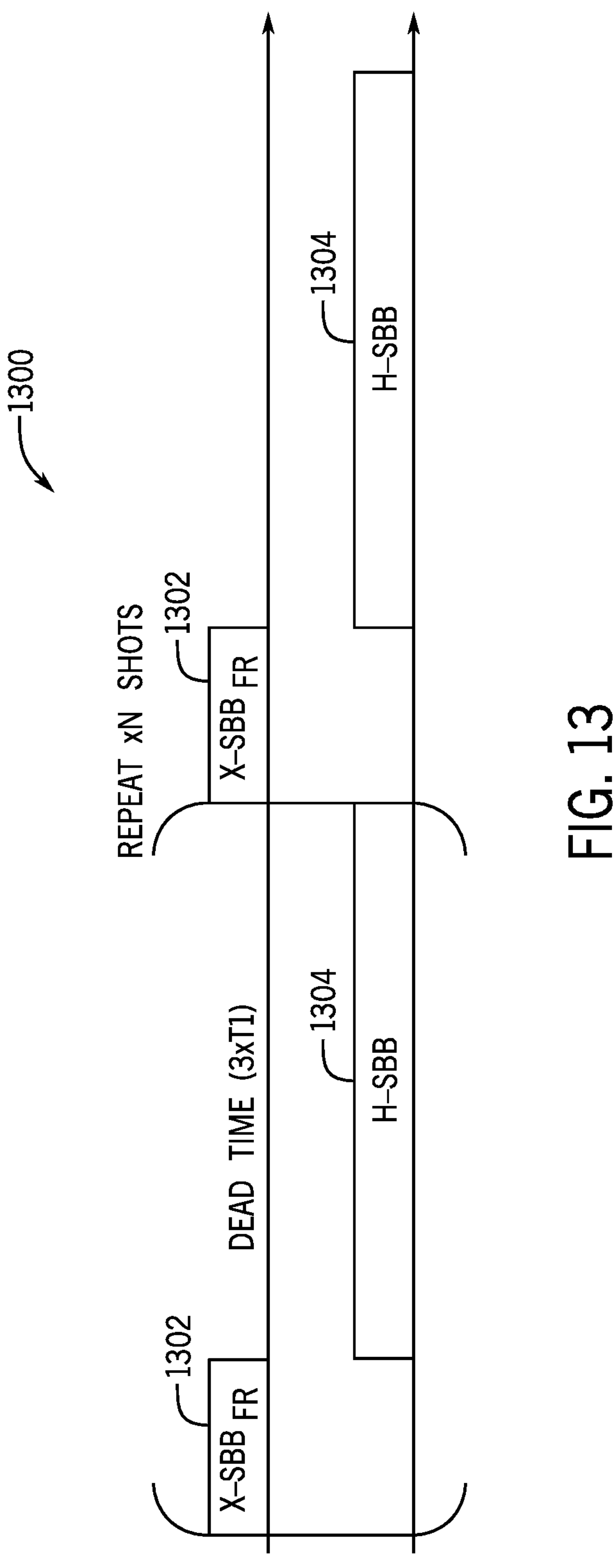
FIG. 13 illustrates an example X-nuclei pulse sequence module and H-nuclei pulse sequence module interleaved acquisition strategy in accordance with an embodiment.
Figure 14:
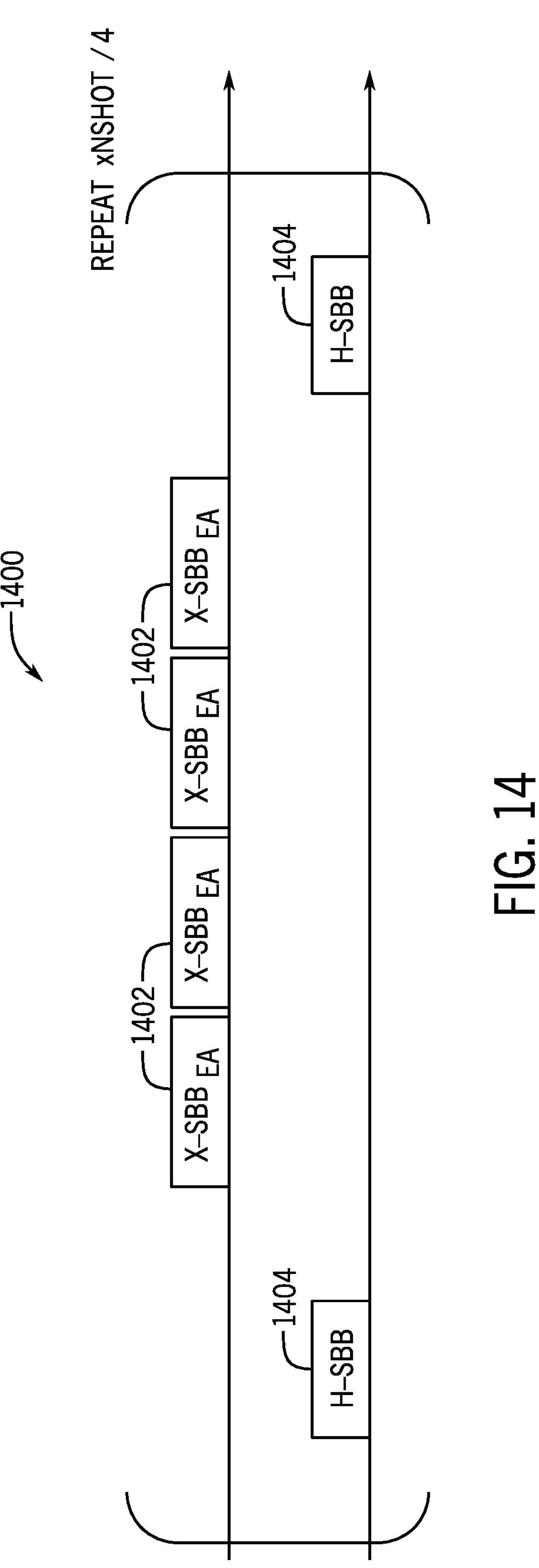
FIG. 14 illustrates an example X-nuclei pulse sequence module and H-nuclei pulse sequence module interleaved acquisition strategy in accordance with an embodiment.
Figure 15:
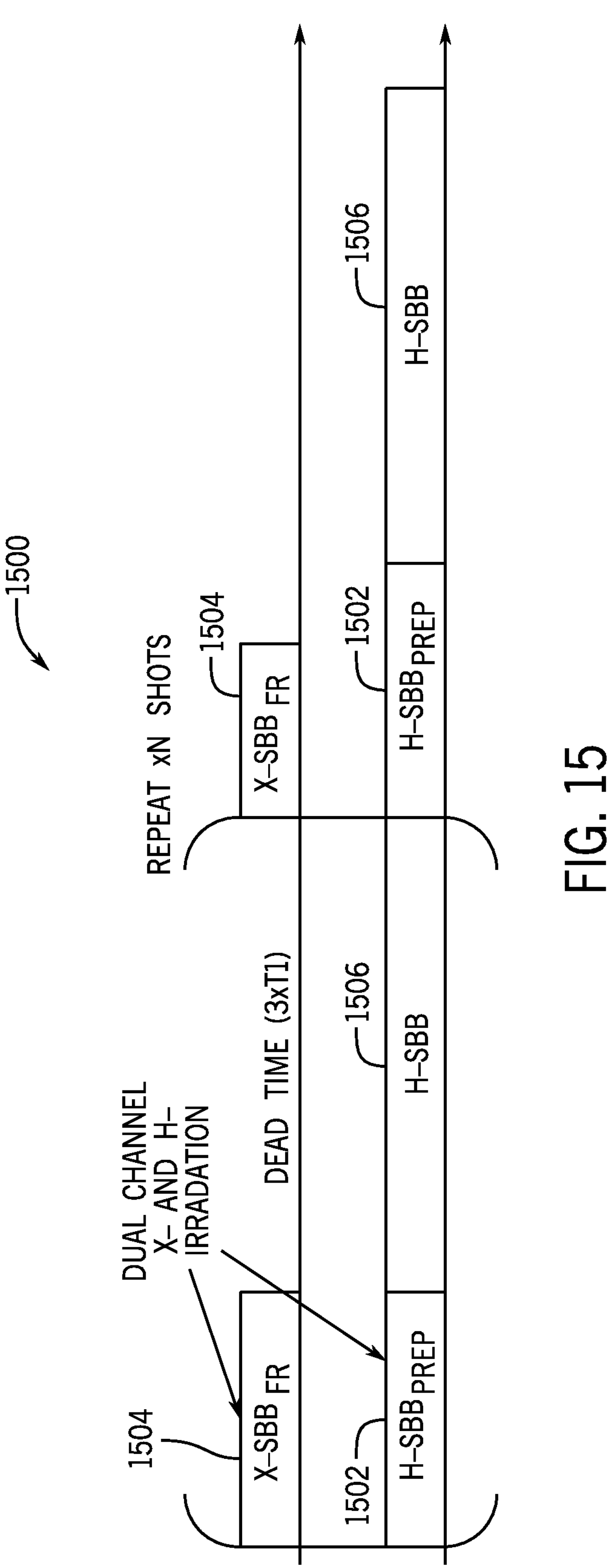
FIG. 15 illustrates an example X-nuclei pulse sequence module and H-nuclei pulse sequence module with magnetization preparation) interleaved acquisition strategy in accordance with an embodiment.

Returning to FIG. 2, at block 206 the H-nuclei (e.g., Na-nuclei) pulse sequence module and the H-nuclei pulse sequence module are repeatedly performed using the MRI system in an interleaved manner. In other words, the Na-nuclei pulse sequence module and the H-nuclei pulse sequence module are interleaved during the scan to acquire both the first set of MR data and the second set of MR data. As mentioned above, the MRI system (e.g., MRI system 100 described above with respect to FIG. 1) is configured to switch between a first RF coil tuned to the X-nuclei and a second RF coil tuned to the H-nuclei. Various examples of interleaved acquisition strategies for X-nuclei and H-nuclei for multinuclear MRI are shown in FIGS. 13-15. In FIG. 13, the interleaved acquisition strategy 1300 includes an X-SBB module 1302 that is fit into multi-slice H-SBB modules 1304. In an embodiment, the H-SBB 1304 may be any proton sequence, or part of a sequence including a single excitation event from a multishot sequence or multiple excitations (shots) from one or more sequences. In the acquisition strategy 1300 of FIG. 13, the interleaved X-SBB 1302 and H-SBB 1304 may be repeated for N shots. In FIG. 14, the interleaved acquisition strategy 1400 includes an X-SBB module 1402 that is fit into multi-slice H-SBB modules 1404. In an embodiment, the H-SBB 1404 may be any proton sequence, or part of a sequence including a single excitation event from a multishot sequence or multiple excitations (shots) from one or more sequences. In the acquisition strategy 1400 of FIG. 14, the interleaved X-SBB 1402 and H-SBB 1404 may be repeated $N_{shot}/4$. In FIG. 15, the interleaved acquisition strategy 1500 includes RF preparatory modules ($H$-$SBB_{Prep}$) 1502, for example, chemical exchange saturation transfer (CEST), magnetization transfer (MT), inversion recovery (IR), or saturation recovery (SR). In the acquisition strategy 1500 of FIG. 15, the alternating between the X-SBB 1504 and the H-SBB 1506 in an interleaved manner may be repeated for N shots.

Referring again to FIG. 2, at block 208 the X-nuclei pulse sequence module and the H-nuclei pulse sequence module are repeatedly performed in an interleaved manner until the acquisition of first set of MR data and the second set of MR data are complete. If the acquisition of the first set of MR data and the second set of MR data are not complete at block 208, the process returns to block 206. If the acquisition of the first set of MR data and the second set of MR data are complete at block 208, at least one X-nuclei (e.g., Na) based image of the region of interest is generated using the first set of MR data at block 210. In an embodiment where the X-nuclei pulse sequence module is a Na-nuclei pulse sequence module, the Na-based image may be, for example, a static sodium image or a sodium TSC variation map may be generated using the first set of MR data. At block 212, at least one H-nuclei based image of the region of interest is generated using the second set of MR data. For example, a $T_2$-weighted image, a diffusion weighted image, a perfusion weighted image, fMRI image, and etc. may be generated using the second set of MR data. At block 214, one or more of the at least one X-nuclei based image and the at least one H-nuclei based image may be displayed on a display (e.g., display 104, 136 or 144 shown in FIG. 1).

Figure 16:
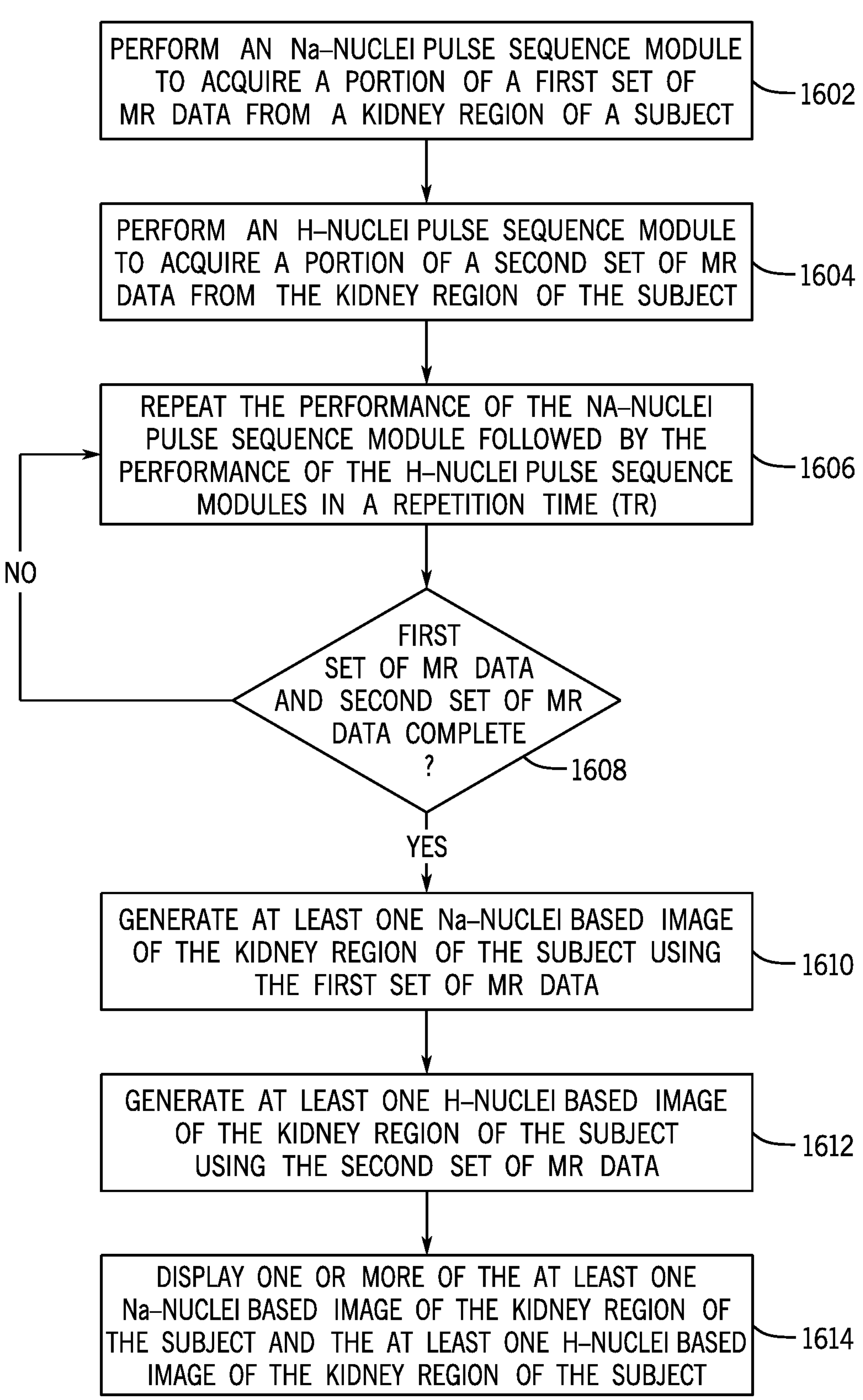
FIG. 16 illustrates a method for multinuclear turbo spin echo MR imaging for generating images of a kidney region of a subject for use in evaluating renal impairment of the subject in accordance with an embodiment.

As mentioned above, the multinuclear sequence with interleaved X-nuclei and H-nuclei modules (or SBBs) may be used in various imaging applications, such as evaluating renal impairment, stroke, epilepsy, and brain tumors. FIG. 16 illustrates a method for multinuclear turbo spin echo MR imaging for generating images of a kidney region of a subject for use in evaluating renal impairment of the subject in accordance with an embodiment. In FIG. 16, the X-nuclei is sodium (Na). In this embodiment, an $Na^+$ Density-Adapted GRE, $Na^+$-$SBB_{DAR}$, module (e.g., $Na^+$-$SBB_{DAR}$ module 300 shown in FIG. 3) is interleaved with an $H^+$ turbo spin echo, $H^+$-$SBB_{TSE}$, module (e.g., $H^+$-$SBB_{TSE}$ module 700 shown in FIG. 7) to acquire a set of MR data to generate Na-nuclei based image(s) and to acquire a set of MR data to generate H-nuclei based MR image(s), respectively, of a kidney region of a subject. At block 1602, an Na-nuclei pulse sequence module (i.e., an $Na^+$-$SBB_{DAR}$ module) may be performed in a first repetition time (TR) using an MRI system (e.g., MRI system 100 described above with respect to FIG. 1) to acquire a portion of a first set of MR data from a kidney region in a subject. In some embodiments, the acquired portion of the first MR data set may be a line of k-space. The portion of the first set of MR data may be acquired using a first RF coil that is tuned to the Na-nuclei. At block 1604, an H-nuclei pulse sequence module (i.e., a $H^+$-$SBB^{TSE}$ module) may be performed in the first repetition time using the MRI system (e.g., MRI system 100 described above with respect to FIG. 1) to acquire a portion of a second set of MR data from the kidney region in the subject. In some embodiments, the portion of the second set of MR data is a shot, plurality or group of k-space lines. The portion of the second set of MR data may be acquired using a second RF coil that is tuned to the H-nuclei.

At block 1606, the $Na^+$-$SBB_{DAR}$ module and the $H^+$-$SBB^{TSE}$ module are repeatedly performed using the MRI system in an interleaved manner. Accordingly, each repetition time (TR) can include performing one $Na^+$-$SBB_{DAR}$ module to acquire a portion of the first set of MR data followed by performing an $H^+$-$SBB_{TSE}$ module to acquire a portion of the second set of MR data. As mentioned, in some embodiments, each TR produces a single line of k-space from the $Na^+$-$SBB_{DAR}$ module and each TR acquires a shot, group or plurality of k-space lines from the $H^+$-$SBB_{TSE}$ module. Accordingly, each TR can be used to cycle through single lines of—space for the first set of MR data acquired using the $Na^+$-$SBB_{DAR}$ module and each TR can be used to cycle through shots or groups of k-space lines using the $H^+$-$SBB_{TSE}$ module. At block 1608, the $Na^+$-$SBB_{DAR}$ module and the $H^+$-$SBB_{TSE}$ module are repeatedly performed in an interleaved manner until the acquisition of first set of MR data and the acquisition of the second set of MR data are complete. If the acquisition of the first set of MR data and the second set of MR data are not complete at block 1608, the process returns to block 1606. If the acquisition of the first set of MR data and the second set of MR data are complete at block 1608, at the end of the acquisition the acquired k-space lines from all TRs (which cycle through k-space) for the first set of MR data may be constructed into at least one Na-nuclei based image, for example, a single static sodium image of the kidney region at block 1610 and the acquired data for the second set of MR data may be constructed into at least one H-nuclei based image, for example, a $T_2$-weighted image of the kidney region at block 1612. At block 1614, one or more of the at least one Na-nuclei based image and the at least one H-nuclei based image may be displayed on a display (e.g., display 104, 136 or 144 shown in FIG. 1). The at least one Na-nuclei based image (e.g., a static sodium image) and the at least one H-nuclei based image (e.g., a $T_2$-weighted image) of the kidney region may be used to evaluate renal impairment of the subject.

Figure 17:
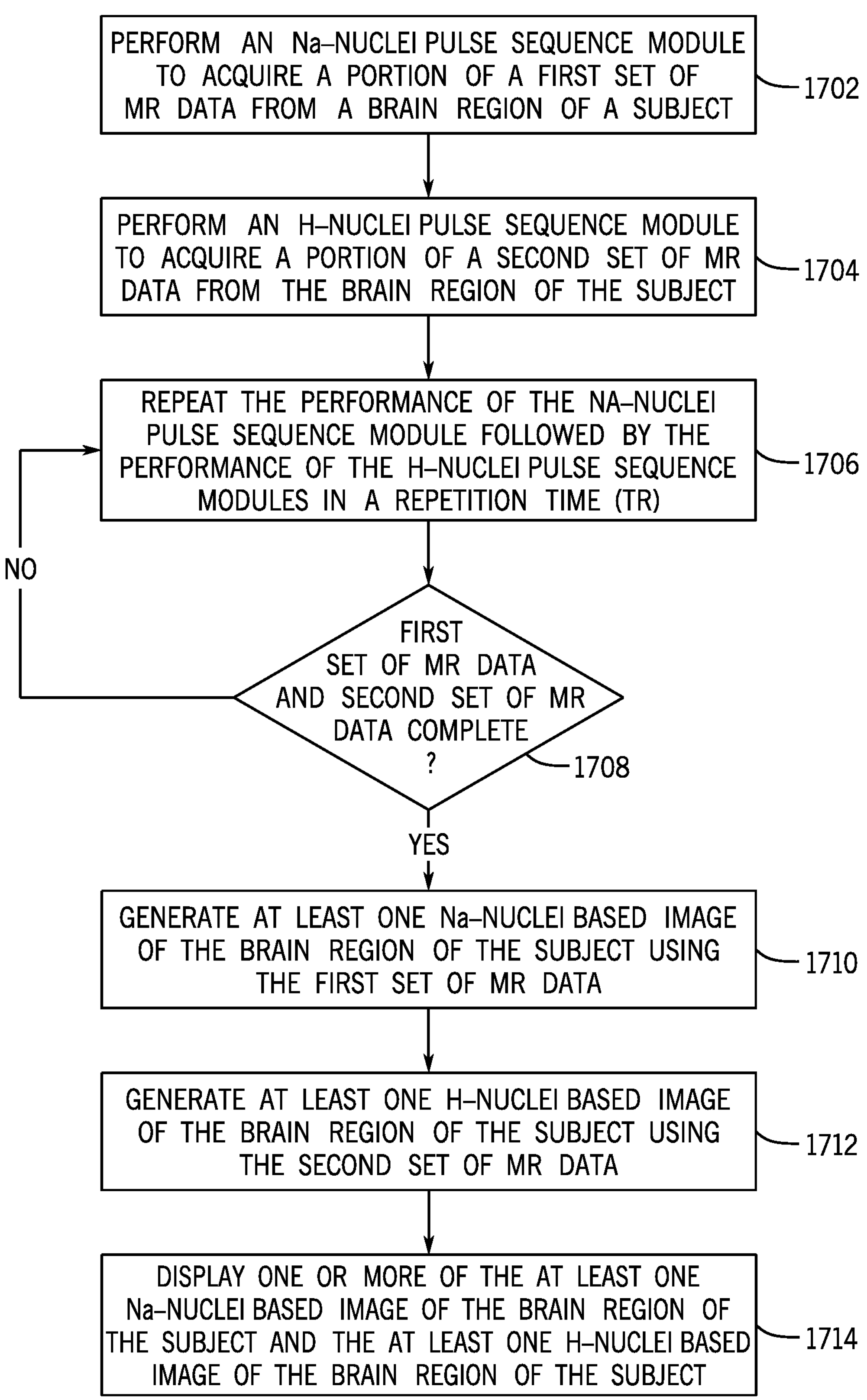
FIG. 17 illustrates a method for multinuclear EPI MR imaging for generating images of a brain of a subject in accordance with an embodiment.

FIG. 17 illustrates a method for multinuclear EPI MR imaging for generating images of a brain of a subject in accordance with an embodiment. In FIG. 17, the X-nuclei is sodium (Na). In some embodiments, the multinuclear EPI MR imaging acquisition may be configured for diffusion MRI and used to evaluate stroke in a subject. In some embodiments, the multinuclear EPI MR imaging acquisition may be configured for dynamic susceptibility contrast (DSC) Perfusion MRI and used to evaluate stroke in a subject. At block 1702, an Na-nuclei pulse sequence module may be performed in a first repetition time (TR) to acquire a portion of a first set of MR data from a brain region in a subject and, at block 1704, an H-nuclei pulse sequence module may be performed in the first repetition time to acquire a portion of a second set of MR data from the brain region in the subject. The Na-nuclei pulse sequence module and H-nuclei pulse sequence module may be performed using an MRI system (e.g., MRI system 100 described above with respect to FIG. 1).

In some embodiments, for diffusion MRI, an $Na^+$ Density-Adapted GRE, $Na^+$-$SBB_{DAR}$, module (e.g., $Na^+$-$SBB_{DAR}$ module 300 shown in FIG. 3) is interleaved with an $H^+$-Diffusion Weighted (DW) EPI, $H^+$-$SBB_{DW-EPI}$, module (e.g., $H^+$-$SBB_{DW-EPI}$ module 1000 shown in FIG. 10) to acquire a set of MR data to generate Na-nuclei based image(s) and to acquire a set of MR data to generate H-nuclei based MR image(s), respectively, of the brain region of the subject. In some embodiments, the portion of the first MR data set acquired using the $Na^+$-$SBB_{DAR}$ module may be a line of k-space. The portion of the first set of MR data may be acquired using a first RF coil that is tuned to the Na-nuclei. In some embodiments, the portion of the second set of MR data acquired using the $H^+$-$SBB_{DW-EPI}$ module is data for a DW direction or b-value. The portion of the second set of MR data may be acquired using a second RF coil that is tuned to the H-nuclei.

In some embodiments, for DSC perfusion MRI, an $Na^+$ Density-Adapted GRE, $Na^+$-$SBB_{DAR}$, module (e.g., $Na^+$-$SBB_{DAR}$ module 300 shown in FIG. 3) is interleaved with an $H^+$-Gradient Echo (GE) Echo Planar Imaging (EPI), $H^+$-$SBB_{GE-EPI}$, module (e.g., $H^+$-$SBB_{GE-EPI}$ module 900 shown in FIG. 9) to acquire a set of MR data to generate Na-nuclei based image(s) and to acquire a set of MR data to generate H-nuclei based MR image(s), respectively, of a brain region of the subject. In some embodiments, the portion of the first MR data set acquired using the $Na^+$-$SBB_{DAR}$ module may be a line of k-space. The portion of the first set of MR data may be acquired using a first RF coil that is tuned to the Na-nuclei. In some embodiments, the portion of the second set of MR data acquired using the $H^+$-$SBB_{GE-EPI}$ module is data for a dynamic time point. Data may be acquired for dynamic time points before and after the injection of a contrast agent in the subject. The portion of the second set of MR data may be acquired using a second RF coil that is tuned to the H-nuclei.

In some embodiments, for evaluating epilepsy, an $Na^+$ Density-Adapted GRE, $Na^+$-$SBB_{DAR}$, module (e.g., $Na^+$-$SBB_{DAR}$ module 300 shown in FIG. 3) is interleaved with an $H^+$-Gradient Echo (GE) Echo Planar Imaging (EPI). $H^+$-$SBB_{GE-EPI}$, module (e.g., $H^+$-$SBB_{GE-EPI}$ in module 900 shown in FIG. 9) to acquire a set of MR data to generate Na-nuclei based image(s) and to acquire a set of MR data to generate H-nuclei based MR image(s), respectively, of the brain region of the subject. In some embodiments, the portion of the first MR data set acquired using the $Na^+$-$SBB_{DAR}$ module may be a line of k-space. In some embodiments, each TR may use a sliding window to acquire dynamic sodium MR data. The portion of the first set of MR data may be acquired using a first RF coil that is tuned to the Na-nuclei. In some embodiments, the portion of the second set of MR data acquired using the $H^+$-$SBB_{GE-EPI}$ module is data for a dynamic time point. The portion of the second set of MR data may be acquired using a second RF coil that is tuned to the H-nuclei.

At block 1706, the Na-nuclei module and the H-nuclei module are repeatedly performed using the MRI system in an interleaved manner. Accordingly, each repetition time (TR) can include performing one Na-nuclei module to acquire a portion of the first set of MR data followed by performing an $H^{-nuclei}$ module to acquire a portion of the second set of MR data. In some embodiments, for diffusion MRI, each repetition time (TR) can include performing one $Na^+$-$SBB_{DAR}$ module to acquire the portion of the first set of MR data followed by performing an $H^+$-$SBB_{DW-EPI}$ module to acquire the portion of the second set of MR data. As mentioned above, for diffusion MRI, each TR can produce a single line of k-space from the $Na^+$-$SBB_{DAR}$ module and each TR can acquire data for a DW direction or b-value from the $H^+$-$SBB_{DW-EPI}$ module. Accordingly, each TR can be used to cycle through single lines of—space for the first set of MR data acquired using the $Na^+$-$SBB_{DAR}$ module and each TR can be used to cycle through data for DW directions or b-values using the $H^+$-$SBB_{DW-EPI}$ module.

In some embodiments, for DSC perfusion MRI, each repetition time (TR) can include performing one $Na^+$-$SBB_{DAR}$ module to acquire the portion of the first set of MR data followed by performing an $H^+$-$SBB_{GE-EPI}$ module to acquire the portion of the second set of MR data. As mentioned above, for DSC perfusion MRI, each TR can produce a single line of k-space from the $Na^+$-$SBB_{DAR}$ module and each TR can acquire data for a dynamic time point from the $H^+$-$SBB_{DW-EPI}$ module. Accordingly, each TR can be used to cycle through single lines of—space for the first set of MR data acquired using the $Na^+$-$SBB_{DAR}$ module and each TR can be used to cycle through data for dynamics time points using the $H^+$-$SBB_{GE-EPI}$ module. As mentioned above, data may be acquired for dynamic time points before and after the injection of a contrast agent in the subject.

In some embodiments, for evaluating epilepsy, each repetition time (TR) can include performing one $Na^+$-$SBB_{DAR}$ module to acquire the portion of the first set of MR data followed by performing an $H_+$-$SBB_{GE-EPI}$ module to acquire the portion of the second set of MR data. As mentioned above, for DSC perfusion MRI, each TR can produce a single line of k-space from the $Na^+$-$SBB_{DAR}$ module and each TR can acquire data for a dynamic time point from the $H^+$-$SBB_{DW-EPI}$ module. Accordingly, each TR can be used to cycle through single lines of—space for the first set of MR data acquired using the $Na^+$-$SBB_{DAR}$ module and each TR can be used to cycle through data for dynamics time points using the $H^+SBB_{GE-EPT}$ module.

At block 1708, the Na-nuclei module and the H-nuclei module are repeatedly performed in an interleaved manner until the acquisition of first set of MR data and the acquisition of the second set of MR data are complete. If the acquisition of the first set of MR data and the second set of MR data are not complete at block 1708, the process returns to block 1706. If the acquisition of the first set of MR data and the second set of MR data are complete at block 1708, the first set of MR data may be constructed into at least one Na-nuclei based image at block 1710 and the acquired data for the second set of MR data may be constructed into at least one H-nuclei based image at block 1712. In some embodiments, for diffusion MRI, at the end of the acquisition the acquired k-space lines from all TRs (which cycle through k-space) for the first set of MR data may be constructed into at least one Na-nuclei based image, for example, a single static sodium image of the brain and the acquired data for all DW directions or b-values from all TRs may be constructed into, for example, a diffusion-weighted image of the brain. In some embodiments, for DSC perfusion MRI, at the end of the acquisition the acquired k-space lines from all TRs (which cycle through k-space) for the first set of MR data may be constructed into at least one Na-nuclei based image, for example, a single static sodium image of the brain and the acquired data for all data from a dynamic time points from all TRs may be constructed into, for example, a $T_2$*-weighted image of the brain. In some embodiments, the generated $T_2$*-weighted images may be used as a dynamic time series of the brain at the end of the acquisition. In some embodiments, for evaluation of epilepsy, at the end of the acquisition the acquired k-space lines from all TRs (which cycle through k-space) for the first set of MR data may be constructed into at least one Na-nuclei based image, for example, a single static sodium image of the brain and the acquired data for all data from a dynamic time points from all TRs may be constructed into, for example, an fMRI image of the brain. In some embodiments, each TR uses a sliding window to acquire dynamic sodium MR data to generate, for example, a sodium TSC variation map.

At block 1714, one or more of the at least one Na-nuclei based image and the at least one H-nuclei based image may be displayed on a display (e.g., display 104, 136 or 144 shown in FIG. 1). In some embodiments, for diffusion MRI, the at least one Na-nuclei based image (e.g., a static sodium image) and the at least one H-nuclei based image (e.g., a diffusion-weighted image) of the brain region may be used to evaluate stroke in the subject. In some embodiments, for DSC perfusion MRI, the at least one Na-nuclei based image (e.g., a static sodium image) and the at least one H-nuclei based image (e.g., a $T_2$*-weighted image) of the brain region may be used to evaluate stroke in the subject. In some embodiments, the at least one Na-nuclei based image (e.g., a static or dynamic sodium image) and the at least one H-nuclei based image (e.g., an fMRI image) of the brain region may be used to evaluate stroke in the subject.

Figure 18:
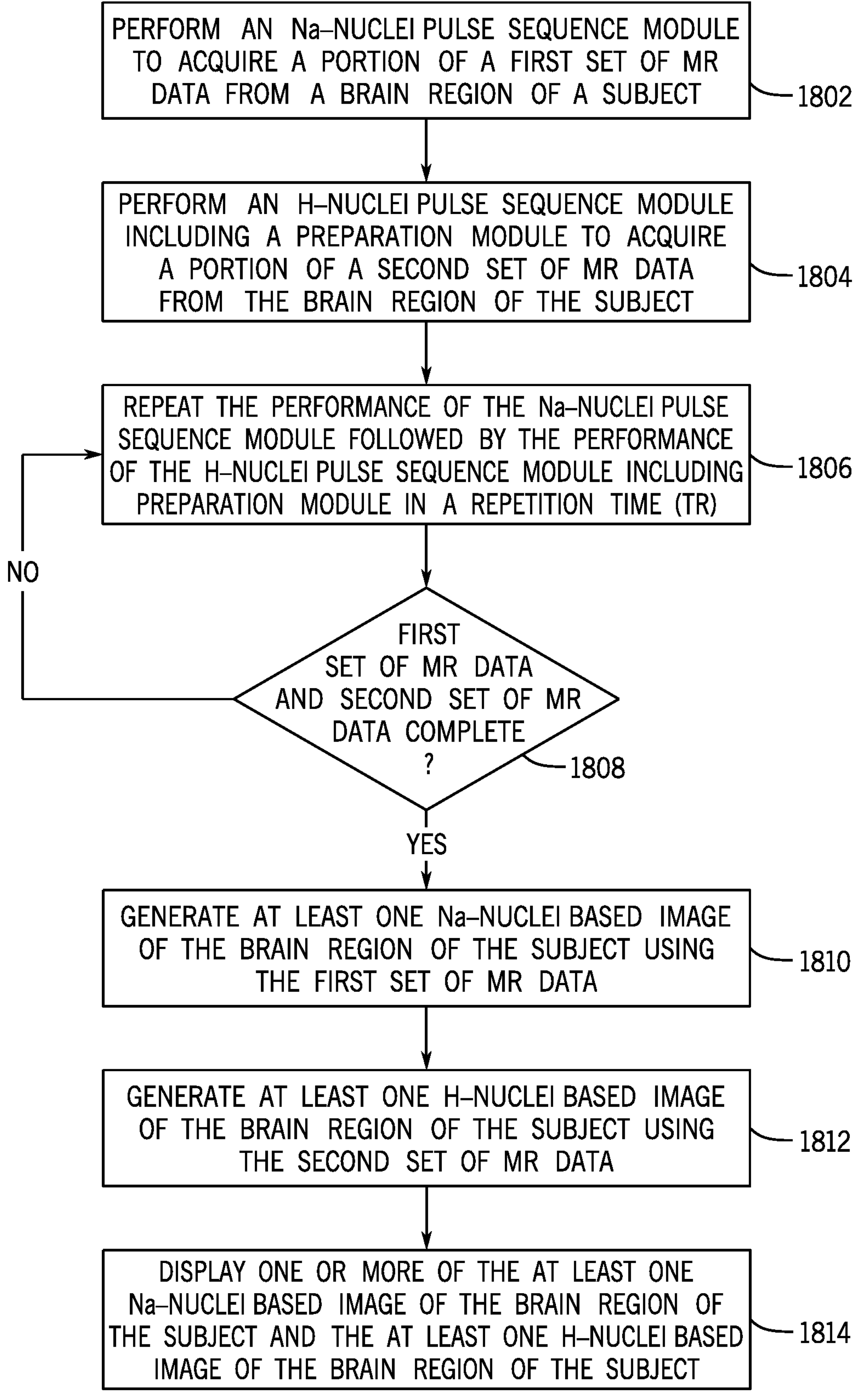
FIG. 18 illustrates a method for multinuclear CEST-SAGE-EPI MR imaging for generating images of a brain in a subject for use in metabolic imaging of brain tumors in the subject in accordance with an embodiment.

FIG. 18 illustrates a method for multinuclear CEST-SAGE-EPI MR imaging for generating images of a brain in a subject for use in metabolic imaging of brain tumors in the subject in accordance with an embodiment. In FIG. 18, the X-nuclei is sodium (Na). In some embodiments, an $Na^+$ Density-Adapted GRE, $Na^+$-$SBB_{DAR}$, module (e.g., $Na^+$-$SBB_{DAR}$ module 300 shown in FIG. 3) is interleaved with an $H^+$-$SBB_{CEST-SAGE-EPI}$ module (e.g., the combination of modules 1100 and 1200 shown in FIGS. 11 and 12, respectively) to acquire a set of MR data to generate Na-nuclei based image(s) and to acquire a set of MR data to generate H-nuclei based MR image(s), respectively, of a brain of a subject. In some embodiments, the Na-nuclei based image may be, for example, a static sodium image of the brain and the H-nuclei based image may be, for example, a metabolic-weighted image. In some embodiments, the multinuclear CEST-SAGE-EPI MR sequence (i.e., a multinuclear $Na^+H^+$ metabolic MR sequence) may be configured to be sensitive to $Na^+$ concentration, tissue pH, and $O_2$ utilization and may be used to acquire $Na^+$-, pH-, and $O_2$-weighted images. For acquisition of $Na^+$-, pH-, and $O_2$-weighted images, the $H^+SBB_{CEST-SAGE-EPI}$ module may be a fast anime proton CEST-SAGE-EPI acquisition. The interleaved $Na^+$-$SBB_{DAR}$ module and $H^+SBB_{CEST-SAGE-EPI}$ module may be used to obtain a set of pH- and $O_2$-sensitive images at the same time as a line of k-space is acquired for $Na^+$ images. For example, the $H^+$-$SBB_{CEST-SAGE-EPI}$ module can be performed during the "dead time" TR or relaxation time required for the $Na^+$ nuclei to return to equilibrium. Conventional methods for acquiring $Na^+$, pH-, and $O_2$-weighted images collect the images sequentially resulting in a total scan time of approximately 30-60 min. Advantageously, in some embodiments, interleaving $Na^+$ and $H^+$-CEST-SAGE-EPI acquisitions can allow $Na^+$-, pH-, and $O^2$ image contrasts to be constructed in approximately 15 minutes, making it clinically and economically feasible.

At block 1802, an Na-nuclei pulse sequence module (e.g., a $Na^+$-$SBB_{DAR}$ module) may be performed in a first repetition time (TR) using an MRI system (e.g., MRI system 100 described above with respect to FIG. 1) to acquire a portion of a first set of MR data from a brain region in a subject. In some embodiments, the acquired portion of the first MR data set using the $Na^+$-$SBB_{DAR}$ module may be a line of k-space. The portion of the first set of MR data may be acquired using a first RF coil that is tuned to the Na-nuclei. At block 1804, an H-nuclei pulse sequence module (i.e., a $H^+$-$SBB_{CEST-SAGE-EPI}$ module) including a preparation module may be performed in the first repetition time using the MRI system (e.g., MRI system 100 described above with respect to FIG. 1) to acquire a portion of a second set of MR data from the brain region in the subject. In some embodiments, the $H^+$-$SBB_{CEST-SAGE-EPI}$ module incudes a $H^+$-$SBB_{CEST-Prep}$ preparation module and a $H^+$-$SBB_{SAGE-EPI}$ module (for example, the combination of modules shown in FIGS. 11 and 12). In some embodiments, the portion of the second set of MR data using the $H^+$-$SBB_{CEST-SAGE-EPI}$ module is data for a CEST z-spectral point. The portion of the second set of MR data may be acquired using a second RF coil that is tuned to the H-nuclei.

At block 1806, the $Na^+$-SBB module and the $H^+$-$SBB_{CEST-SAGE-EPI}$ module are repeatedly performed using the MRI system in an interleaved manner. Accordingly, each repetition time (TR) can include performing one $Na^+$-$SBB_{DAR}$ module to acquire a portion of the first set of MR data followed by performing an $H^+SBB_{CEST-SAGE-EPI}$ module to acquire a portion of the second set of MR data. As mentioned, in some embodiments, each TR produces a single line of k-space from the $Na^+$-SBB module and each TR acquires a CEST z-spectral point from the $H^+$-$SBB_{CEST-SAGE-EPI}$ module. Accordingly, each TR can be used to cycle through single lines of—space for the first set of MR data acquired using the $Na^+$-SBB module and each TR can be used to cycle through data for CEST z-spectral points (or the CEST z-spectrum) using the $H^+$-$SBB_{CEST-SAGE-EPI}$ module. In some embodiments for acquisition of $Na^+$, pH-, and $O_2$-weighted images, during each effective repetition time ($TR_{eff}$) or epoch, the technique will cycle through lines of k-space for the $Na^+$nuclei while cycling through z-spectral RF offset frequencies for the $H^+$ nuclei.

At block 1808, the $Na^+$-SBB module and the $H^+$-$SBB_{CEST-SAGE-EPI}$ module are repeatedly performed in an interleaved manner until the acquisition of first set of MR data and the acquisition of the second set of MR data are complete. If the acquisition of the first set of MR data and the second set of MR data are not complete at block 1808, the process returns to block 1806. If the acquisition of the first set of MR data and the second set of MR data are complete at block 1808, at the end of the acquisition the acquired k-space lines from all TRs (which cycle through k-space) for the first set of MR data may be constructed into at least one Na-nuclei based image, for example, single static sodium image of the brain at block 1810 and the acquired data for the second set of MR data may be constructed into at least one H-nuclei based image, for example, a metabolic-weighted image of the brain at block 1812. In some embodiments, the at Na-nuclei based image(s) can include a static $Na^+$ image (NaT) and the H-nuclei image(s) can include pH- and $O_2$-weighted images (e.g., $MTR_{asym}$ at 3 ppm and $R_2'$, respectively). In some embodiments, an AGI may be constructed and fused with the NaT image, resulting in estimates of:

$$eNHE1 = \frac{MTR_{asym}3ppm \cdot rCBV \cdot NaT}{R_2'} \quad \text{Eqn. 3}$$

where rCBV is relative cerebral blood volume. Accordingly, the disclosed acquisition technique can allow for the construction of $Na^+$-. pH-, and $O_2$-weighted MR images simultaneously. In some embodiments, advantageously the $Na^+$. pH-, and $O_2$-weighted MR images can be constructed with no added contrast or risk to patients. Known methods may be used to generate or calculate the various types of Na-nuclei and H-nuclei images (e.g., static sodium image, pH-weighted image, $O_2$-weighted image, etc.) from the acquired MR data.

At block 1814, one or more of the at least one Na-nuclei based image and the at least one H-nuclei based image may be displayed on a display (e.g., display 104, 136 or 144 shown in FIG. 1). The at least one Na-nuclei based image (e.g., a static sodium image) and the at least one H-nuclei based image (e.g., a metabolic-weighted image) of the kidney region may be used to evaluate brain tumor of the subject Computer-executable instructions for multinuclear MRI using interleaved X-nuclei and H-nuclei modules (or SBBs) according to the above-described methods may be stored on a form of computer readable media. Computer readable media includes volatile and nonvolatile, removable, and non-removable media implemented in any method or technology for storage of information such as computer readable instructions, data structures, program modules or other data. Computer readable media includes, but is not limited to, random access memory (RAM), read-only memory (ROM), electrically erasable programmable ROM (EEPROM), flash memory or other memory technology, compact disk ROM (CD-ROM), digital volatile disks (DVD) or other optical storage, magnetic cassettes, magnetic tape, magnetic disk storage or other magnetic storage devices, or any other medium which can be used to store the desired instructions and which may be accessed by a system (e.g., a computer), including by internet or other computer network form of access.

The present invention has been described in terms of one or more preferred embodiments, and it should be appreciated that many equivalents, alternatives, variations, and modifications, aside from those expressly stated, are possible and within the scope of the invention.

The invention claimed is:

1. A method for multinuclear magnetic resonance imaging (MRI) of a kidney region of a subject using an MRI system, the method comprising:

performing, using the MRI system, a Na-nuclei pulse sequence module during a first repetition time to acquire a portion of a first set of MR data from the kidney region of the subject;

performing, using the MRI system, an H-nuclei pulse sequence module during the first repetition time to acquire a portion of a second set of MR data from the kidney region of the subject;

repeating, using the MRI system, the performing of the Na-nuclei pulse sequence module and the H-nuclei pulse sequence module in an interleaved manner during a plurality of subsequent repetition times until acquisition of the first set of MR data and the second set of MR data are complete, wherein both the Na-nuclei pulse sequence module and the H-nuclei pulse sequence module are performed in each subsequent repetition time;

generating, using a processor, at least one Na-based image using the first set of MR data;

generating, using the processor, at least one H-base image using the second set of MR data; and displaying one or more of the at least one Na-based image and the at least one H-based image on a display.

2. The method according to claim 1, wherein the Na-nuclei pulse sequence module is a Na density adapted gradient echo (DAR) pulse sequence module.

3. The method according to claim 1, wherein the H-nuclei pulse sequence module is a turbo spin echo (TSE) pulse sequence module.

4. The method according to claim 1, wherein one or more of the at least one Na-based image and the at least one H-based image includes information related to renal impairment of the subject.

5. The method according to claim 1, wherein the portion of the first set of MR data is a line of k-space and the portion of the second set of MR data is a plurality of lines of k-space.

6. A method for multinuclear magnetic resonance imaging (MRI) of a brain region of a subject using an MRI system, the method comprising:

performing, using the MRI system, a Na-nuclei pulse sequence module during a first repetition time to acquire a portion of a first set of MR data from the brain of the subject;

performing, using the MRI system, an H-nuclei pulse sequence module during the first repetition time to acquire a portion of a second set of MR data from the brain of the subject;

repeating, using the MRI system, the performing of the Na-nuclei pulse sequence module and the H-nuclei pulse sequence module in an interleaved manner during a plurality of subsequent repetition times until acquisition of the first set of MR data and the second set of MR data are complete, wherein both the Na-nuclei pulse sequence module and the H-nuclei pulse sequence module are performed in each subsequent repetition time;

generating, using a processor, at least one Na-based image using the first set of MR data;

generating, using the processor, at least one H-base image using the second set of MR data; and displaying one or more of the at least one Na-based image and the at least one H-based image on a display.

7. The method according to claim 6, wherein the Na-nuclei pulse sequence module and the H-nuclei pulse sequence module are configured for diffusion MRI.

8. The method according to claim 7, wherein the Na-nuclei pulse sequence module is a Na density adapted gradient echo (DAR) pulse sequence module.

9. The method according to claim 7, wherein the H-nuclei pulse sequence module is a diffusion MRI pulse sequence module.

10. The method according to claim 6, wherein the Na-nuclei pulse sequence module is a Na density adapted gradient echo (DAR) pulse sequence module.

11. The method according to claim 6, wherein the H-nuclei pulse sequence module is a gradient echo EPI pulse sequence module.

12. The method according to claim 6, wherein the Na-nuclei pulse sequence module and the H-nuclei pulse sequence module are configured for DSC perfusion MRI.

13. The method according to claim 6, wherein one or more of the at least one Na-based image and the at least one H-based image includes information related to stroke.

14. The method according to claim 6, wherein one or more of the at least one Na-based image and the at least one H-based image includes information related to epilepsy.

15. A method for multinuclear magnetic resonance imaging (MRI) of a brain region of a subject using an MRI system, the method comprising:

performing, using the MRI system, a Na-nuclei pulse sequence module during a first repetition time to acquire a portion of a first set of MR data from the brain of the subject;

performing, using the MRI system, an H-nuclei pulse sequence module during the first repetition timer to acquire a portion of a second set of MR data from the brain of the subject, wherein the H-nuclei pulse sequence module includes a preparation module;

repeating, using the MRI system, the performing of the Na-nuclei pulse sequence module and the H-nuclei pulse sequence module in an interleaved manner during a plurality of subsequent repetition times until acquisition of the first set of MR data and the second set of MR data are complete, wherein both the Na-nuclei pulse sequence module and the H-nuclei pulse sequence module are performed in each subsequent repletion time;

generating, using a processor, at least one Na-based image using the first set of MR data;

generating, using the processor, at least one H-based image using the second set of MR data; and displaying one or more of the at least one Na-based image and the at least one H-based image on a display.

16. The method according to claim 15, wherein the Na-nuclei pulse sequence module is a Na density adapted gradient echo (DAR) pulse sequence module.

17. The method according to claim 15, wherein the wherein the H-nuclei pulse sequence module is a Spin and Gradient Echo (SAGE) Echo Planar Imaging (EPI) pulse sequence module.

18. The method according to claim 17, wherein the preparation module is a chemical exchange saturation transfer (CEST) preparation module.

19. The method according to claim 15, wherein one or more of the at least one Na-based image and the at least one H-based image includes information related to a brain tumor.

20. The method according to claim 15, wherein the at least one Na-based image includes a static sodium image and the at least one H-based image includes a pH-weighted image and an $O_2$-weighted image.

* * * * *